United States Patent
Chauveau

(10) Patent No.: US 8,360,580 B2
(45) Date of Patent: Jan. 29, 2013

(54) METHOD OF MEASURING THE POSITION, IN A HORIZONTAL DIRECTION IN THE SAGITTAL PLANE, OF A REMARKABLE POINT OF AN EYE OF A SUBJECT

(75) Inventor: Jean-Pierre Chauveau, Charenton le Pont (FR)

(73) Assignee: Essilor International (Compagnie Generale d'Optique), Charenton-le-Pont (FR)

(*) Notice: Subject to any disclaimer, the term of this patent is extended or adjusted under 35 U.S.C. 154(b) by 119 days.

(21) Appl. No.: 12/593,694

(22) PCT Filed: Mar. 26, 2008

(86) PCT No.: PCT/FR2008/000412
§ 371 (c)(1),
(2), (4) Date: Sep. 29, 2009

(87) PCT Pub. No.: WO2008/132356
PCT Pub. Date: Nov. 6, 2008

(65) Prior Publication Data
US 2010/0128220 A1    May 27, 2010

(30) Foreign Application Priority Data
Mar. 30, 2007  (FR) .................. 07 02335

(51) Int. Cl.
*A61B 3/00* (2006.01)
*A61B 3/10* (2006.01)
*A61B 3/14* (2006.01)
(52) U.S. Cl. ......... 351/246; 351/204; 351/206; 351/208
(58) Field of Classification Search .......... 351/204–206, 351/208, 211, 246, 209
See application file for complete search history.

(56) References Cited

U.S. PATENT DOCUMENTS

| | | | |
|---|---|---|---|
| 3,454,331 A | | 7/1969 | Maitenaz |
| 5,016,282 A | * | 5/1991 | Tomono et al. ............... 382/117 |
| 6,580,448 B1 | | 6/2003 | Stuttler |
| 7,434,935 B2 | * | 10/2008 | Bonnin ......................... 351/246 |
| 7,783,077 B2 | * | 8/2010 | Miklos et al. ................. 351/209 |
| 7,434,935 B2 | * | 10/2008 | Bonnin ......................... 351/246 |
| 7,783,077 B2 | * | 8/2010 | Miklos et al. ................. 351/209 |

FOREIGN PATENT DOCUMENTS

DE     102004020356     11/2005
(Continued)

OTHER PUBLICATIONS

International Search Report dated Oct. 13, 2008 in PCT application.

*Primary Examiner* — Ricky Mack
*Assistant Examiner* — Zachary Wilkes
(74) *Attorney, Agent, or Firm* — Young & Thompson

(57) ABSTRACT

The present invention relates in general to taking geometrico-morphological measurements on a subject. More particularly, the invention relates to a method of measuring the position of a remarkable point of the subject's eye. The method includes amongst others, the steps of capturing images in different relative postures (APIV1, APIV2, (O1,X1,Y1,Z1), (O2,X2,Y2,Z2)) of a subject, identifying reference points of the eye ((RCG1, RCD1), (RCG2, RCD2)), and calculating the remarkable point (CROD, CROG) as a function of the captured images. The values of the posture parameter (APIV) are obtained by a position-identification element (60, 70, 80, 700, 800) having at least one known geometrical characteristic that is placed on the subject's head. Each captured image contains a representation of the position-identification element (60, 70, 80, 700, 800). The posture parameter is thus calculated as a function of these images and of the known geometrical characteristic.

21 Claims, 7 Drawing Sheets

FOREIGN PATENT DOCUMENTS

| | | |
|---|---|---|
| DE | 102005003699 | 7/2006 |
| EP | 1747750 | 1/2007 |
| WO | 0209025 | 1/2002 |
| WO | WO 2005070284 A1 * | 8/2005 |
| WO | 2006029875 | 3/2006 |
| WO | 2006106248 | 10/2006 |

* cited by examiner

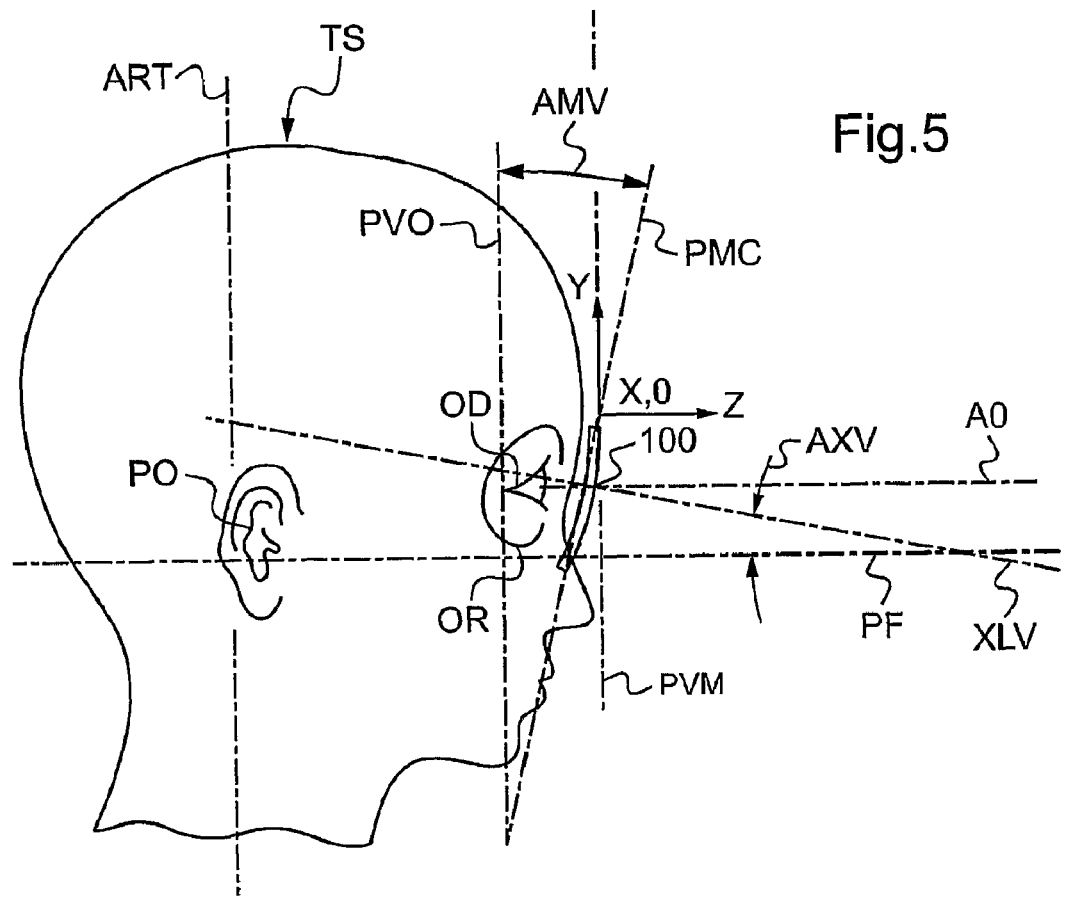
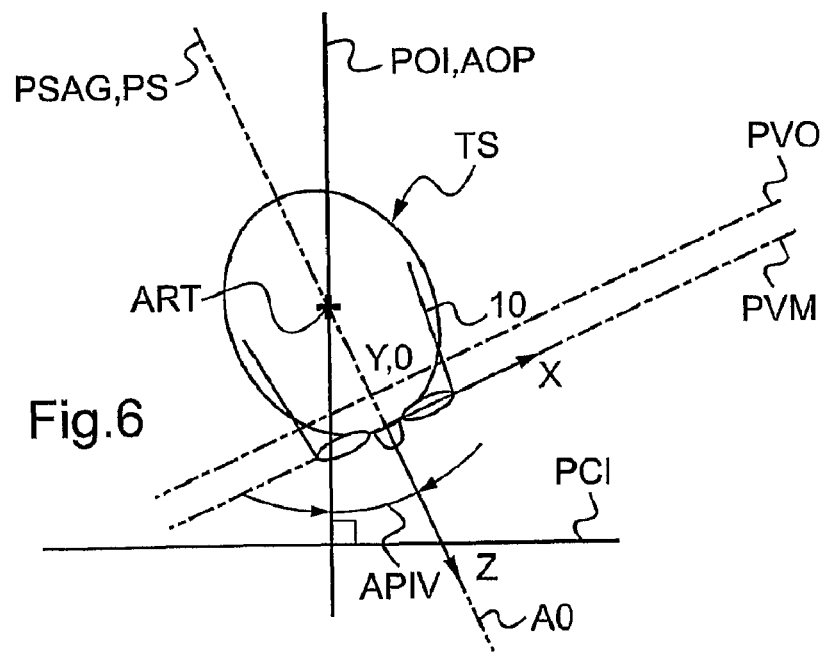

METHOD OF MEASURING THE POSITION, IN A HORIZONTAL DIRECTION IN THE SAGITTAL PLANE, OF A REMARKABLE POINT OF AN EYE OF A SUBJECT

TECHNICAL FIELD TO WHICH THE INVENTION RELATES

The present invention relates in general to taking geometrico-morphological measurements of a subject. More particularly, the invention relates to a method of measuring the position of a remarkable point of an eye of the subject. A particular, but non-exclusive, application of the invention lies in taking geometrico-morphological measurements on a future wearer of eyeglasses for the purpose of personalizing the optical design of the corrective ophthalmic lenses that are to be mounted in the frame selected by said future wearer.

TECHNOLOGICAL BACKGROUND

When optically designing a corrective ophthalmic lens, attempts are made nowadays to take better account of individual geometrico-morphological parameters associated with the wearer and with the selected frame, with this being referred to as "personalized" optical design. These parameters comprise in particular the three-dimensional configuration of the lens relative to the wearer's head, under wearing conditions. This three-dimensional configuration is determined: i) by the orientation of the lens relative to the corresponding eye of the wearer; and ii) by the distance between the lens and the corresponding eye of the wearer.

In order to determine this three-dimensional configuration, the optician places a pair of presentation lenses on the wearer's nose. The presentation lenses comprise the frame selected by the wearer, together with non-corrective lenses that are mounted in the rims of the frame.

The distance between each lens and the corresponding eye of the wearer is measured manually: the optician observes the wearer in profile and estimates a measurement of the distance between the cornea and the rear face of the presentation lens, with the help of a small ruler.

Proposals have been made to automate this measurement by photographing the wearer in profile and processing the image acquired in that way in an attempt to determine the distance between the lens and the eye. Nevertheless, the operation of processing the image has been found to be unreliable, insofar as the rims and the temples of the frame can mask the eye, and insofar as recognizing the point on the rear face of the lens that faces the eye is found to be risky. Furthermore, taking a profile image of the wearer is in addition to taking other geometrico-morphological measurements of the wearer, such as measuring the pupillary distance and the heights of the eyes, the curvature of the frame, the pantoscopic angle of each lens when worn (i.e. the angle formed between the general plane of the lens and the vertical), or indeed the visual behavior of the wearer (in particular the wearer's tendency to move the eyes or the head to a greater or a lesser extent when scrutinizing a field of view). Unfortunately, all or some of those other measurements can be performed by taking one or more images of the wearer in face view. The Applicant has therefore set out, in the context of the present invention, to propose a method that enables the distance between the eye and the lens to be measured on the basis of images that are generally face views and not profile views.

Furthermore, the distance between the pupil and the rear face of the lens is not the magnitude that is the most pertinent when calculating a personalized optical design by ray tracing for the corrective lens that is to be fitted to the frame. Movement of the eye can generally be considered as being a combination of rotations about a particular point that is referred to as the center of rotation of the eye (CRO). It is the position of this point that the designer of the lens desires to know in order to perform calculations properly. In present practice, the position of the CRO is deduced approximately from the position of the cornea by assuming a mean value for the radius of the eye, typically a value of about 15 millimeters (mm). Unfortunately, the radius of the eye varies significantly from one individual to another, such that this approximation leads to significant errors that are highly penalizing for the pertinence of the personalized optical design calculation.

OBJECT OF THE INVENTION

The object of the present invention is to remedy the above-mentioned drawbacks in full or in part.

To this end, the present invention provides a method of measuring the position, in a horizontal direction of the sagittal plane, of a remarkable point of an eye of a subject in a frame of reference associated with the head of said subject, the method being characterized in that it comprises the steps of:

S1) arranging the subject's head in a first relative posture relative to the entry pupil of an image capture appliance placed facing the subject's face;

S2) in said first relative posture, capturing a first plane image of the eye by means of the image capture appliance;

S3) in said first image, identifying the image of a first predetermined reference point of the eye;

S4) arranging the subject's head in a second relative posture relative to the entry pupil of the image capture appliance, the second relative posture being distinct from the first relative posture;

S5) in the second relative posture, capturing a second plane image of the eye by means of the image capture appliance;

S6) in said second image, identifying the image of a second predetermined reference point of the eye; and S9) calculating said position of the remarkable point of the eye as a function of the images of the first and second reference points of the eye and of the first and second values of a posture parameter associated respectively with the first and second relative postures, said values of the posture parameter being calculated using the following steps:

placing a position-identification element on the head of the subject, said element having at least one known geometrical characteristic;

for each of the first and second plane images captured in each relative posture by means of the image capture appliance incorporating a plane image of the plane position-identification element, processing said image to measure a geometrical characteristic depending on the known geometrical characteristic of the position-identification element; and calculating the different values of the posture parameter for the different postures as a function of said measured geometrical characteristic of the captured image of the position-identification element and of the known geometrical characteristic of the position-identification element.

The comparison between the images of the first and second reference points of the eye is representative of the apparent angular movement of the eye starting from the two different viewpoints corresponding to the first and second relative postures. The looked-for position can then be found by a parallax calculation, given the information about the two viewpoints as constituted by the first and second values for the posture parameter.

Furthermore, the method of the invention can be implemented with the help of a single image capture appliance.

Finally, the posture parameters corresponding to each posture of the subject are calculated on the basis solely of plane images captured in face view in the different postures, without any other measurements being performed.

Advantageously, the remarkable point having the looked-for position is the center of rotation of the subject's eye.

While capturing the first and second images, provision can then be made for the eye to look respectively at first and second sighting points having positions that are known relative to each other, for the position of the center of rotation of the subject's eye in the frame of reference associated with the subject to be calculated also as a function of the relative positions of the sighting points, and for the first and second postures and the first and second sighting points to be chosen so that, when capturing the first and second images, the corresponding directions of the gaze of the eye are distinct in the frame of reference associated with the subject's head.

The positions of the first and second sighting points relative to the pupil of the image capture appliance may be distinct, or on the contrary they may coincide.

According to another advantageous characteristic of the invention, in order to calculate the position of the remarkable point of the eye in step S9), the following substeps are performed:

from the image of the first reference point of the eye and from the first value of the posture parameter, deducing the coordinates, in said frame of reference of the subject's head, of a first observation straight line connecting the pupil of the image capture appliance and the first reference point of the eye;

from the image of the second reference point of the eye and from the second value of the posture parameter, deducing the coordinates in said frame of reference of the subject's head, of a second observation straight line connecting the pupil of the image capture appliance and the second reference point of the eye; and calculating the position of the remarkable point of the subject's eye in the frame of reference associated with the subject's head as a function of the coordinates of the first and second observation straight lines.

Then, advantageously, the remarkable point of position that is looked for is the center of rotation of the subject's eye, and the position of said point is calculated as the position of the point of intersection of the two observation straight lines, or if said straight lines do not intersect accurately, the point where said observation straight lines come closest together.

By way of example, the posture parameter may consist in one or more of the following parameters:

the horizontal angle (i.e. the angle in a horizontal plane) between the image capture appliance and the subject's head;

the vertical angle (i.e. the angle in a vertical plane) between the image capture appliance and the subject's head; and the distance between the image capture appliance and the subject's head.

By way of example, the first and second reference points of the eye may coincide at a common point of the eye consisting in one of the following points of the eye:

the center of the pupil or of the iris; and a point of the sclera adjacent to the canthus or to the upper or lower edge of the eyelid.

The first and second reference points of the eye may also be points of the eye that are distinct from each other.

The remarkable point of looked-for position may, for example, consist in one of the following points of the eye:

the center of the pupil or of the iris; and a point of the sclera adjacent to the canthus or to the upper or lower edge of the eyelid.

Provision can then advantageously be made for the first and second reference points of the eye to coincide with the remarkable point of said eye having the looked-for position.

According to yet another advantageous characteristic of the invention, during steps S1) and S4), the subject's head is arranged relative to the entry pupil of the image capture appliance in the first and second relative postures in such a manner that the position of the pupil of the image capture appliance relative to a vertical axis of rotation of the subject's head is not modified between said first and second postures by a transverse movement of more than 200 millimeters in a direction perpendicular to the optical axis of the image capture appliance, and in such a manner that the subject pivots the head about said vertical axis of rotation through at least 5 degrees and not more than 60 degrees between said first and second postures in order to gaze respectively at the first and second sighting points that have different positions that are known relative to each other.

This combination of characteristics solves the above-explained additional technical problem concerning obtaining two different relative postures of the subject's head relative to the entry pupil of the image capture appliance.

To ensure that the subject's head is arranged in two different postures relative to the entry pupil of the image capture appliance, it is possible to proceed in various ways.

If the image capture appliance is movable, it is possible to move the image capture appliance between capturing the first and second images, with the vertical axis of rotation of the subject's head remaining stationary. The subject's head pivots about this vertical axis of rotation so that the subject's eyes gaze on the pupil of the image capture appliance after it has been moved. Under such circumstances, the optician needs to ensure that the entire face of the wearer is visible in the image captured by the image capture appliance and that the relative height and inclination adjustments between the wearer's head and the image capture appliance have indeed been performed. These operations limit the speed with which images can be captured and also limit their accuracy.

If the image capture appliance presents an identical position while capturing both the first and the second images, the optician may ask the subject to move while gazing at the entry pupil of the image capture appliance. The positioning recommendations given by the optician to the subject ensure that the wearer's face remains visible in each image captured by the image capture appliance. The complex and time-consuming interactions between the subject and the optician nevertheless limit the speed with which the first and second images can be captured.

The two postures of the subject's head relative to the pupil of the image capture appliance can be obtained in simpler and faster manner if the position of the pupil of the image capture appliance and relative to the vertical axis of rotation of the subject's head remains substantially identical while the first and second images are being captured, with only the subject's head turning about said vertical axis of rotation while gazing at first and second positions of a sighting point of the image capture appliance.

These positioning recommendations given by the optician to the subject, and more generally the interactions between the optician and the subject are then limited. Furthermore, the optician can capture an image with better accuracy, since there is no need, between capturing two images, to make successive adjustments to the relative height or inclination between the subject and the image capture appliance, or more generally to picture framing so that the subject's head remains visible in the captured image.

DETAILED DESCRIPTION OF AN EMBODIMENT

The following description with reference to the accompanying drawings given by way of non-limiting example makes it clear what the invention consists in and how it can be reduced to practice.

In the accompanying drawings:

FIG. 5 is a profile view of the head of a wearer fitted with presentation eyeglasses in an orthostatic configuration;

FIG. 6 is a plan view of the wearer fitted with the presentation eyeglasses in a posture in which the head is turned through a certain angle relative to the image capture appliance;

Figure 1:
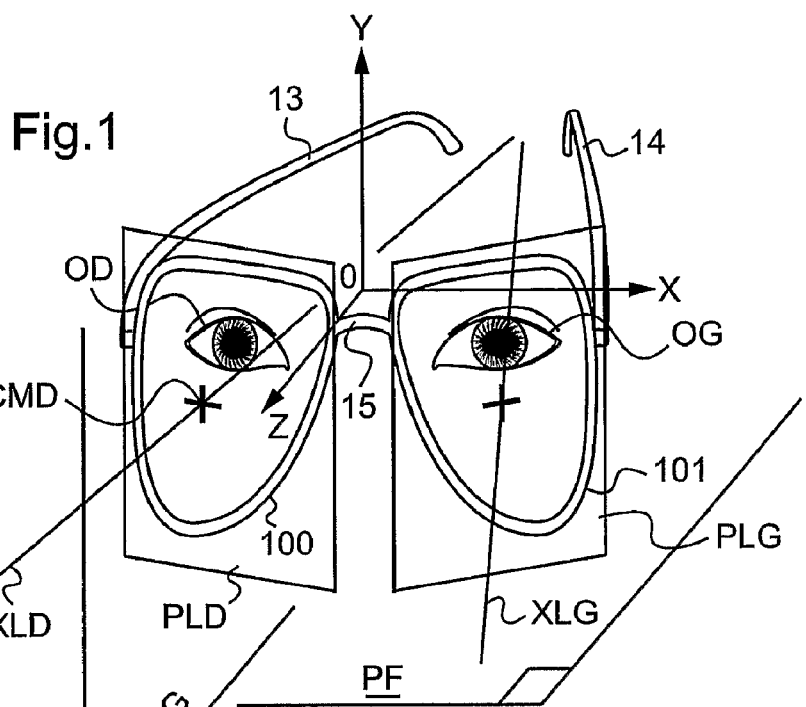
FIG. 1 is a perspective view of a pair of presentation eyeglasses placed in front of the eyes of a future wearer.

In the description below, the optician determines the reference configuration for each corrective ophthalmic lens (not shown) that is to be mounted in an eyeglass frame 10 in a frame of reference associated with the wearer's head, and in the wearing configuration. This configuration is used to implement a personalized optical design method for the corrective ophthalmic lens by calculating shapes for one and/or the other of the optically useful faces of the lens, and/or calculating index gradients of the lens, as a function of the frame of reference of the lens relative to the frame of reference of the wearer.

The wearer is in a sitting or standing configuration that is such that the wearer's head is straight, i.e. the Frankfort plane PF associated with the wearer's head is substantially horizontal. As shown in FIG. 5, the Frankfort plane PF is defined as being the plane containing the bottom orbit point OR and the porion PO of the wearer, where the porion is the highest point in the skull of the acoustic meatus, which corresponds to the tragion of the ear. The wearer's gaze axis is the primary gaze axis, i.e. the wearer is looking at the horizon straight ahead. It is also said that the wearer is taking up an "orthostatic" position, a position requiring least effort.

A sagittal plane PSAG is defined as being the vertical plane containing the right bisector AO between the two eyes OG and OD. The right bisector AO between the eyes is the axis passing through the middle of the segment defined by the centers of rotation CROG, CROD of the two eyes and parallel to the Frankfort plane PF. An eye vertical plane PVO is also defined as being the vertical plane passing through the centers CROG and CROD of the eyes.

The configuration desired for the frame of reference of each corrective lens is determined by:
 the orientation of each corrective lens for mounting on the frame relative to the head of the wearer; and
 the distance in the wearing configuration between the lens and the corresponding eye of the wearer along a horizontal direction of the sagittal plane PSAG (direction of the axis Z as defined below).

The frame of reference of each corrective lens is obtained in this example by determining the configuration of the frame of reference of each of the non-corrective presentation lenses 100, 101 that is fitted to the frame for sales and measurement-taking purposes and that takes the place of the corrective lens that is to be designed when determining geometrico-morphological parameters relating to the wearer and to the frame.

The pair of presentation eyeglasses comprises the frame 10 selected by the wearer and right and left presentation lenses 100 and 101 (non-corrective lenses). In the example shown, the pair of eyeglasses is of the rimmed type, i.e. the lenses are mounted in rims 11 and 12 of the frame 10. In a variant, the pair of presentation eyeglasses could be of the pierced type, i.e. the lenses are pierced, and each is held by one end of a nose bridge and by one of end of the temple associated with the lens, which bridge and temples co-operate with drilled holes.

Device

Figure 2:
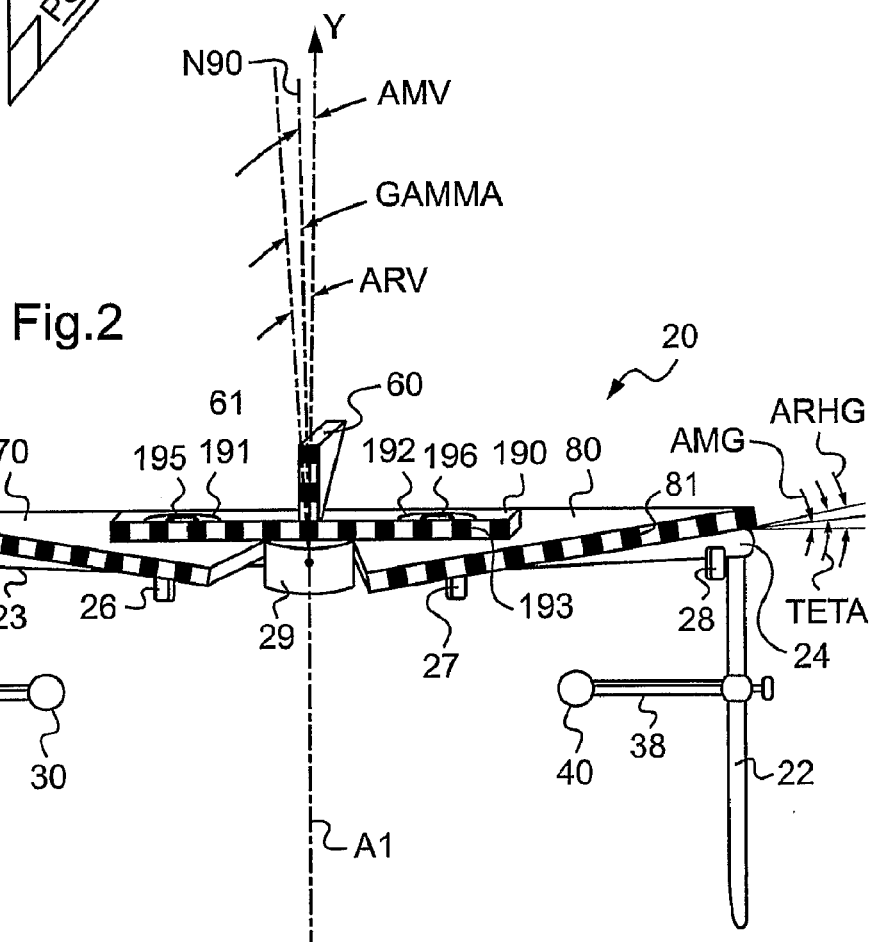
FIG. 2 is a perspective view of a position-identification system for fitting to the pair of presentation eyeglasses.
Figure 3:
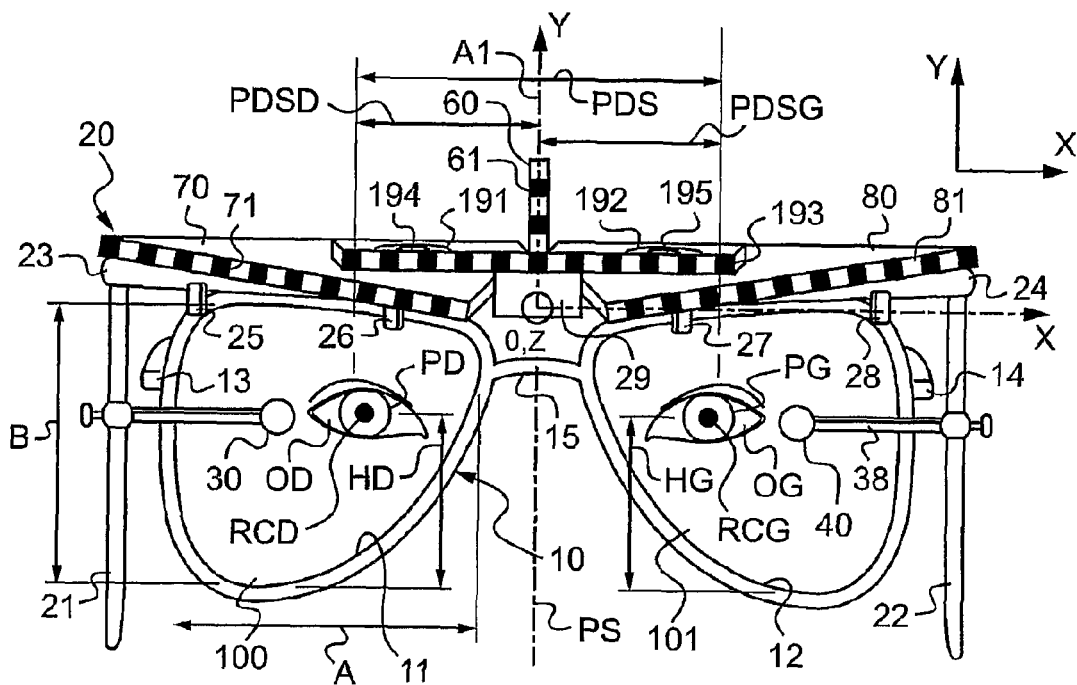
FIG. 3 is a diagrammatic view of the image of the presentation eyeglasses and of the position-identification system in face view.
Figure 4:
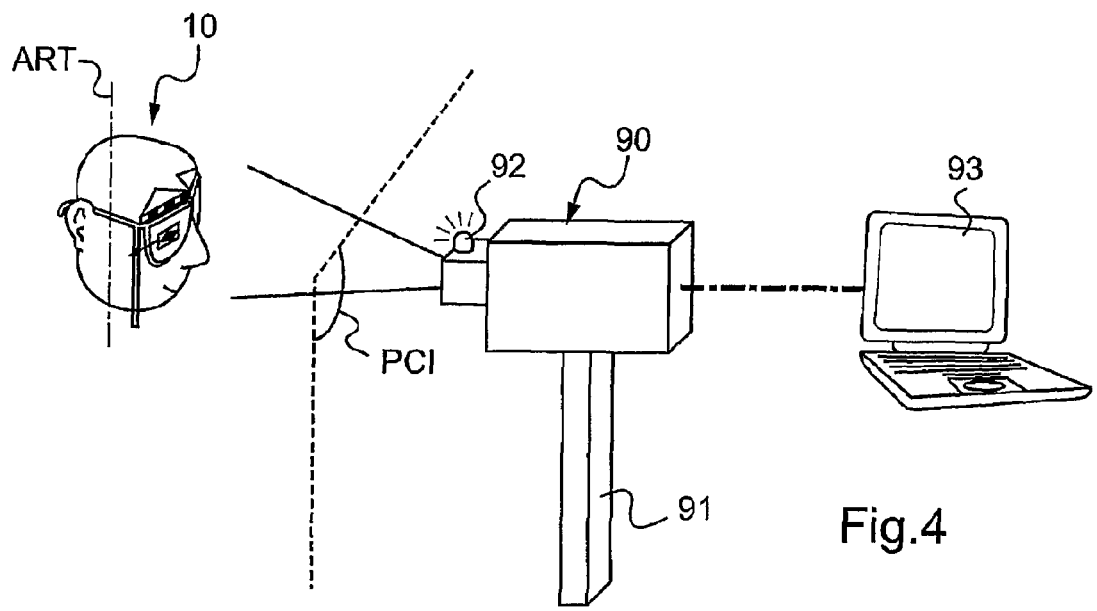
FIG. 4 is a perspective view of the position-identification system of FIG. 2 fastened on the pair of presentation eyeglasses, together with image capture means that communicate with a processor and calculation system.

FIGS. 2 to 4 show a device for determining individual geometrico-morphological parameters of a wearer wearing a pair of presentation eyeglasses. These parameters include the configuration of the frame of reference of each corrective lens that is to be designed relative to the head of the wearer, together with other geometrico-morphological parameters concerning index-gradient distribution and as mentioned below.

The device includes a position-identification system 20 for mounting on the frame 10, and image capture means 90 for acting in an image capture facial plane PCI to capture an image of the position-identification system 20 mounted on the frame 10 in the wearing position. The image capture means 90 are connected to a processor and calculation system 93 for acting on the captured image.

The position-identification system 20 includes a hinged linkage having two sticks 23 and 24 that are substantially rectilinear and substantially coplanar, which sticks are connected together by a hinge 29 presenting a hinge axis A1 that is substantially vertical in the wearing configuration.

Each stick 23, 24 is provided with fastener means, here in the form of a pair of clips 25, 26, 27, and 28. These clips serve to fasten each stick 23, 24 with capacity for pivoting on the substantially horizontal top portion of the rim 11, 12 of the frame (FIG. 3), or when the eyeglasses of the pierced type, of the presentation lens.

Each stick 23, 24 is surmounted by a horizontal position-identification element 70, 80 in the form of a triangular plate of a certain thickness, with an edge face that presents a geometrical pattern 71, 81 designed so that the geometrical configuration of the geometrical pattern 71, 81, when projected onto said image capture facial plane PCI, is representative of the horizontal component of the orientation of said horizontal position-identification element 70, 80. The horizontal component of the orientation of an element is defined by the angle made between the longitudinal direction of said element relative to the eye vertical plane PVO in projection onto the Frankfort plane PF. Similarly, the vertical component of the orientation of an element is defined as the angle made by the longitudinal direction of said element relative to the eye vertical plane PVO in projection onto the sagittal plane PSAG.

In this example, the geometrical pattern comprises repeated motifs at a known spacing that are constituted by dark bands alternating with pale portions so as to obtain sufficient contrast. The motifs of the geometrical pattern 71, 81 extend in the longitudinal direction of the corresponding edge face of the horizontal position-identification element 70, 80. Each dark band is thus substantially vertical in the wearing configuration.

Each horizontal position-identification element 70, 80 is fastened to the corresponding stick 23, 24 in such a manner that firstly the edge face carrying the geometrical pattern 71, 81 is visible in face view, and secondly the long direction of said geometrical pattern (i.e. the longitudinal direction of the corresponding edge face) forms an angle TETA [theta] in the horizontal plane or Frankfort plane PF of about 30 degrees relative to the longitudinal direction of the stick 23, 24 (i.e. the straight line passing through the fastener clips).

The two horizontal position-identification elements 70, 80 are also interconnected by a middle position-identification element 190 that is mechanically associated with the two horizontal position-identification elements 70 and 80 so as to remain constantly in a fixed position relative to a vertical midplane of symmetry of these two elements 70 and 80 that coincides substantially with a plane of symmetry PS of the frame (itself coinciding substantially with the sagittal plane PSAG of the wearer). This middle position-identification element carries a known geometrical pattern presenting an image, when seen in projection on the image capture plane PCI by the image capture means 90, that makes it possible in combination with the images of the position-identification elements 70 and 80 to identify in three dimensions the orientation and the position of the position-identification system 20, as explained in greater detail below.

Specifically, this middle position-identification element is constituted by a holder bar 190 having a longitudinal direction that is substantially perpendicular to the plane of symmetry PS, and thus to the sagittal plane PSAG. Two oblong slots 191 and 192 are formed in the holder bar 190 extending along the longitudinal direction of the bar. The slots 191 and 192 receive two guide studs 195 and 196 attached to the top faces of the position-identification elements 70 and 80. The position-identification means 70 and 80 can therefore slide relative to the holder bar 190 along the longitudinal direction of the bar, with the studs 195 and 196 guiding the movement of the position-identification means 70 and 80 along the slots.

This freedom of the position-identification means 70 and 80 to move in sliding relative to the holder bar 190, in combination with their freedom to move in pivoting about the pivot axis A1, enables the horizontal position-identification elements 70 and 80 to be fastened without stress on the rims 11 and 12 by means of the sticks 23 and 24 so as to be free to follow the longitudinal component of the orientation of the rims 11 and 12 of the frame 10.

On its edge face that faces the image capture means 90, the holder bar 190 also includes a geometrical pattern 193 constituted by dark bands spaced apart from one another by a known distance. As explained below, these dark bands can be used for calculating the distance between the position-identification system 20 and the image capture means 90, and thus for determining the scale factor of the captured image.

Centering means are also provided that enable the position-identification system 20 to be centered on the plane of symmetry PS of the frame in such a manner that the nose bridge 15 is centered on the axis A1.

The position-identification system 20 also includes a vertical position-identification element 60 that is likewise constituted by a triangular plate of a given thickness that extends in a plane substantially perpendicular to the mean plane of the two horizontal position-identification elements 70 and 80 that are associated with the lenses 100 and 101. On that one of its edge faces that is to face towards the image capture means 90, this position-identification element 60 presents a geometrical pattern 61 constituted by geometrical motifs that, as above, are dark bands separated from one another by a known distance and that extend in the longitudinal direction of the corresponding edge face of the position-identification element 60. As a result, in the wearing configuration, each dark band is disposed substantially horizontally and the longitudinal direction of the geometrical pattern 61 is substantially vertical.

The vertical position-identification element 60 is fastened to the top face of the holder bar 190 in its center. The edge face of the element 60 carrying the geometrical pattern 61 lies in a plane that is substantially parallel to the line joining together the centers of rotation CROG and CROD of the eyes and that forms a constant angle GAMMA in the sagittal plane PSAG of 30 degrees relative to the normal N90 to the plane of the top face of the holder bar 190 (FIG. 2).

Close to the free ends of the sticks 23 and 24, there are provided two uprights 21 and 22 that are mutually parallel and that are perpendicular to the sticks 23 and 24. In the wearing configuration, the uprights 21 and 22 are substantially vertical. When the position-identification system 20 is fastened on the frame, the uprights 21 and 22 are situated beside the right and left temples of the wearer, close to the temples 13 and 14 of the frame 10 (see FIG. 3).

Two horizontal rods 37 and 38 are mounted to slide along the uprights 21 and 22. Each rod has a bearing bead 30, 40 at its end that extends towards the other rod. The structure of the position-identification system 20 is designed in such a manner that gravity causes the bearing beads 30 and 40 to bear against the presentation lenses 100 and 101 when the position-identification system 20 is mounted on the frame 10 placed on the wearer's nose. This bearing by gravity is obtained by designing the position-identification system in such a manner that its center of gravity is situated forwards, i.e. beside the geometrical patterns. It is also possible to ballast the fronts of the triangular plates 70, 80. In a variant, in order to press the beads 30 and 40 against each of the lenses, it is possible to provide resilient return means urging the rods 37 and 38 or the uprights 21 and 22 rearwards. Urging the beads 30 and 40 to bear against the corresponding presentation lenses 100 and 101 serves to embody a respective general plane for each of the lenses.

Typically, the image capture means 90 comprise a digital camera that is portable or that is mounted on a support or stand.

The image capture means 90 preferably include a light-emitting diode (LED) 92 that serves firstly to obtain a corneal reflection that is easily identified in the captured image, and secondly to attract the wearer's gaze towards the LED, which is in a known position. This makes it easier to process the captured image.

In this example, the processor and calculation system 93 that acts on the acquired image comprises a microcomputer having installed thereon software for processing the acquired image. In a variant, it is preferable to provide for the processor and calculation system to be an independent system that includes firstly a display screen for communicating the results obtained, and secondly connections enabling the results to be communicated to other appliances. With an independent processor system, provision may also be made for the system to be optionally incorporated in the image capture means 90.

Method

The above-described determination device serves to implement the following method for determining the configuration of the frame of reference of each corrective lens for mounting in the eyeglass frame relative to the frame of reference of the wearer.

As shown in FIG. 4, the optician positions the pair of presentation eyeglasses surmounted by the position-identification system 20 on the wearer's nose. The wearer is in a sitting or standing configuration and the wearer's head is straight, i.e. the Frankfort plane PF is substantially horizontal.

As shown in FIG. 3, the two fastener clips 25 and 26 of the stick 23 are applied onto the top portion of the right rim 11 of the frame 10. Similarly, the two fastener clips 27 and 28 of the stick 24 are applied onto the top portion of the left rim 12 of the frame 10. The fastener clips 25 & 26 and 27 & 28 of each pair are preferably spaced apart as far as possible from each other so that the corresponding stick 23 or 24 follows the horizontal component of the orientation of the rim 11, 12 on which it is fastened. The horizontal component orientation of each rim corresponds overall to the inclination of the associated presentation lens relative to the sagittal plane, in projection onto the Frankfort plane.

The holder bar 190 serves to ensure that the two horizontal position-identification elements 70 and 80 remain substantially coplanar. As a result the vertical position-identification element 60 does indeed extend in the plane of symmetry PS of the frame (and thus in the sagittal plane PSAG) when the position-identification system 20 is mounted on the frame 10 (see FIGS. 3 and 5).

Each bearing bead 30, 40 carried by its height-adjustable rod 37, 38 is placed by the optician substantially level with the corresponding pupils PG, PD of the eyes. The position-identification system 20 is designed in such a manner that the beads 30, 40 bear against the front faces of the presentation lenses 100, 101 under gravity. The beads 30, 40 bearing under gravity against the corresponding presentation lenses 100, 101 rely on the sticks 23, 24 tilting about a tilt axis that is substantially parallel to the axis passing through the centers of the two pupils (and thus substantially perpendicular to the sagittal plane PSAG and parallel to the axis X as defined below). The fastener clips thus act as hinges enabling the position-identification system to tilt about the tilt axis.

As a result, the normal N90 to the plane of the top face of the holder bar 190 follows the vertical component of the orientation of the plane 10, corresponding generally to the angle of inclination in the sagittal plane PSAG of the mean plane of the rims of the frame relative to the eye vertical plane PVO (FIG. 5).

The two points where the fastener clips 25, 26 bear against the rim 11, the frame 10, and the bearing point of the bead 30 on the presentation lens 100 (i.e. the point where the mounting cross is located) define a mean plane PLD of the presentation lens 100 that is associated with the mean plane of the corrective lens in the wearing configuration (FIGS. 1 and 3). The mean plane PLG of the presentation lens 101 is similarly defined passing via the two bearing points of the fastener clips 27, 28 on the rim 12, the frame 10, and the bearing point of the bearing bead 40 against the presentation lens 101.

As shown in FIG. 1, a frame of reference associated with the frame (and thus indirectly with the wearer's head) is defined having an orthogonal system of axes (O,X,Y,Z) and embodied by the position-identification system 20. The center O of this frame of reference is the middle of the segment interconnecting the fastener clips 26 and 27. The axis X is horizontal and passes via the clips 26 and 27. The axis Y is perpendicular to the Frankfort plane, and thus vertical in this example. The plane OYZ is thus vertical and corresponds to the sagittal plane PSAG and also to the plane of symmetry PS. The axis OZ is parallel to the right bisector AO of the eyes. The plane OXZ is parallel to the Frankfort plane PF and is thus horizontal in this example. The plane OXY is referred to as the frame vertical plane PVM and is substantially parallel to the image capture facial plane PCI.

Determining the Orientation of Each Lens Relative to the Corresponding Eye of the Wearer The orientation of each lens is given by the components, in the (O,X,Y,Z) frame of reference, of the vector that is normal to the plane tangential to the lens at the point of the mounting cross CMG, CMD. This mounting cross corresponds to the point of the lens that should be situated facing the pupil of the wearer's eye so that the lens accurately performs the optical correction functions for which it is designed. The vertical component of the orientation of the lens corresponds to the angle formed by the axis or vector that is normal to the plane of the lens relative to the facial plane, in projection onto the sagittal plane. The horizontal component of the orientation of the lens is also defined and corresponds to the angle formed by the axis or vector that is normal to the plane of the lens relative to the facial plane in projection onto the Frankfort plane.

It is desired to determine the orientations of the planes PLG and PLD so as to determine the orientation of each corrective lens that is to be made relative to the frame of reference of the wearer. For this purpose, the orientations are determined of the axes XLG and XLD that pass through the bearing points of the beads 30 and 40 on the presentation lenses 100 and 101 and that are normal to the planes PLG and PLD.

Figure 7:
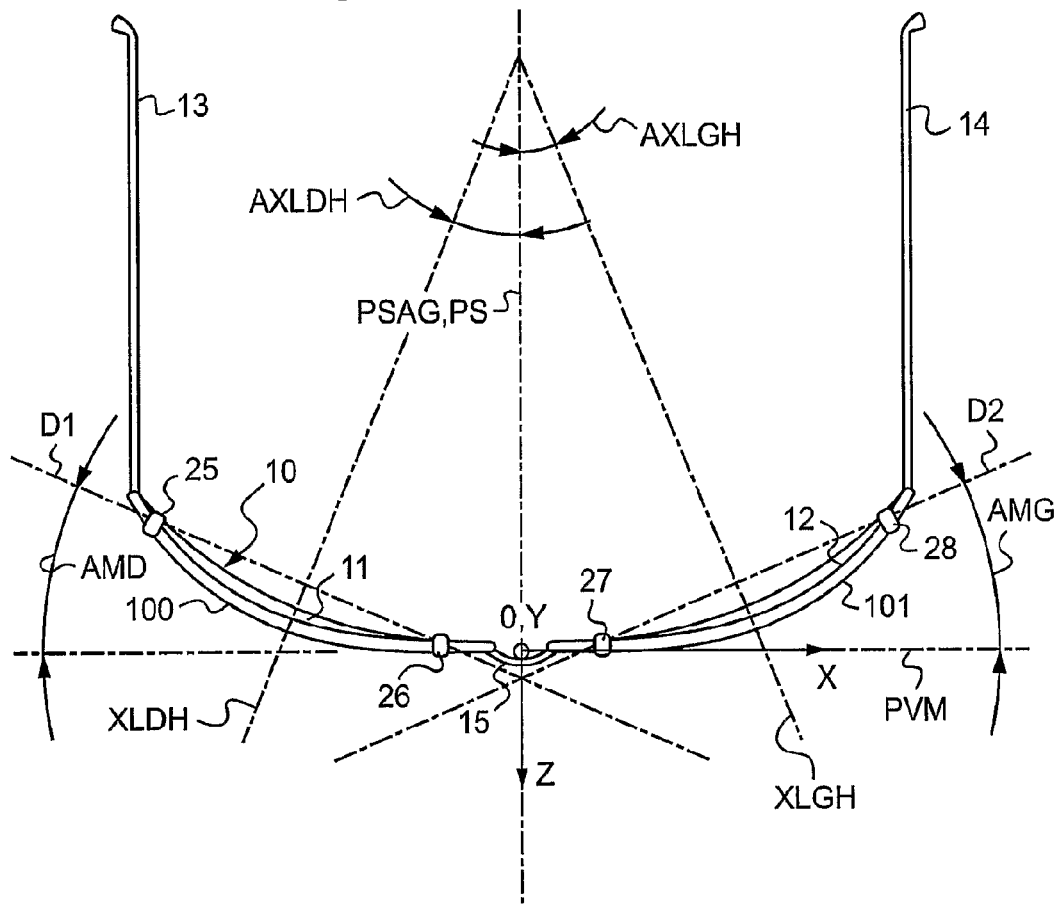
FIG. 7 is a plan view of the frame fitted with the presentation lenses.

As shown in FIG. 7, axes XLGH and XLDH are defined as being the projections onto the horizontal plane or onto the Frankfort plane of the axes XLG and XLD. Likewise, axes XLV are defined as the projections of the axes XLG and XLD onto the sagittal plane (FIG. 5). In this example, it is considered that the projections onto the sagittal plane of the axes XLG and XLD both give rise to the same projected axis XLV. In a variant, it is possible to distinguish between the two projections of the axes XLG and XLD onto the sagittal plane.

The horizontal component of the orientation of each lens 100 or 101 thus corresponds to the angle AXLGH or AXLDH formed by the axis XLGH or XLDH with the sagittal plane PSAG of the wearer's head. Likewise, the vertical component of the orientation of each lens 100 or 101 corresponds to the angle AXV formed by the axis XLV with the Frankfort plane. It then remains to determine the angles AXLGH, AXLDH, and AXV in order to determine the orientation of each lens relative to the wearer.

The angle AXLDH formed between the axis XLDH and its projection onto the sagittal plane PSAG corresponds substantially to the angle AMD formed in the horizontal plane, or Frankfort plane PF, between firstly the straight line D1 passing via the fastener clips 25 and 26 situated on the right rim 11 respectively close to the right temple 13 and to the nose bridge 15, and secondly the vertical plane PVM of the frame. Similarly, the angle AXLGH corresponds substantially to the angle AMG formed firstly between the straight line D2 passing via the fastener clips 27 and 28 situated on the left rim 12 close to the nose bridge 15 and to the left temple 14, and secondly the vertical plane PVM of the frame. To determine each of the angles AXLGH and AXLDH, it thus suffices to determine the angles AMG and AMD.

As shown in FIG. 5, the angle AXV is substantially equal to the angle AMV that is formed in projection onto the sagittal plane PSAG between firstly the eye vertical plane PVO and secondly the mean plane PMC of the two lenses 100 and 101 (or indeed the two rims 11 and 12 of the frame 10). In order to determine the angle AXV it thus suffices to determine the angle AMV.

The optician positions the portable image capture appliance 90 facing the wearer's head and captures in the image capture plane PCI the image of the wearer's head wearing the pair of presentation lenses carrying the position-identification system 20. The image that is obtained corresponds to the image of FIG. 3. Image capture is typically performed in an image capture plane PCI at a distance from the wearer that lies in the range 50 centimeters (cm) to 120 cm. This image capture plane PCI is facial, i.e. substantially parallel to the planes PVO and PVM (FIGS. 4 and 5).

As shown in FIG. 2, the angle ARHD is defined as being the angle formed in the horizontal plane or Frankfort plane PF between firstly the vertical plane PVM and secondly the longitudinal direction of the geometrical pattern 71. When this angle ARHD varies, the spacing between the dark bands also varies in projection in the image capture plane PCI. This angle ARHD is equal to the sum of the angle AMD plus the constant angle TETA of 30 degrees. The angle ARHD thus varies in the same way as the angle AMD. The same applies for the horizontal position-identification element 80 for which the angle ARHG is defined as being the sum of the angle AMG plus the constant angle TETA of 30 degrees.

The processor and calculation system 93 measures the difference between the dark bands of the geometrical pattern 71 of the horizontal position-identification element 70 in the image it has captured in the wearing configuration. To limit measurement errors on the captured image due to the pixels of the captured image, the processor and calculation system 93 measures the spacings between the bands in pairs and takes the average of said spacings. Then, by comparing with a reference configuration of the geometrical pattern 71 for which the angle ARHD and the spacing between the bands are known, it determines the variation in band spacing between the wearing configuration and the reference configuration. Thereafter, the processor and calculation system 93 determines the angle ARHD as a function of this spacing variation. The angle AMD is then determined on the basis of the angle ARHD.

In order to make a valid comparison of the spacings between the bands, the processor and calculation system needs to take account of the scale factor of the captured image. Knowledge of the scale factor enables the band spacing values as measured on the captured image and the reference band spacing values to be reduced to a common scale in order to be able to compare the band spacings. This scale factor is determined from the distance between the position-identification system and the image capture means 90.

The separation distance, referenced D, may be obtained by the calculation method described below.

Figure 8:
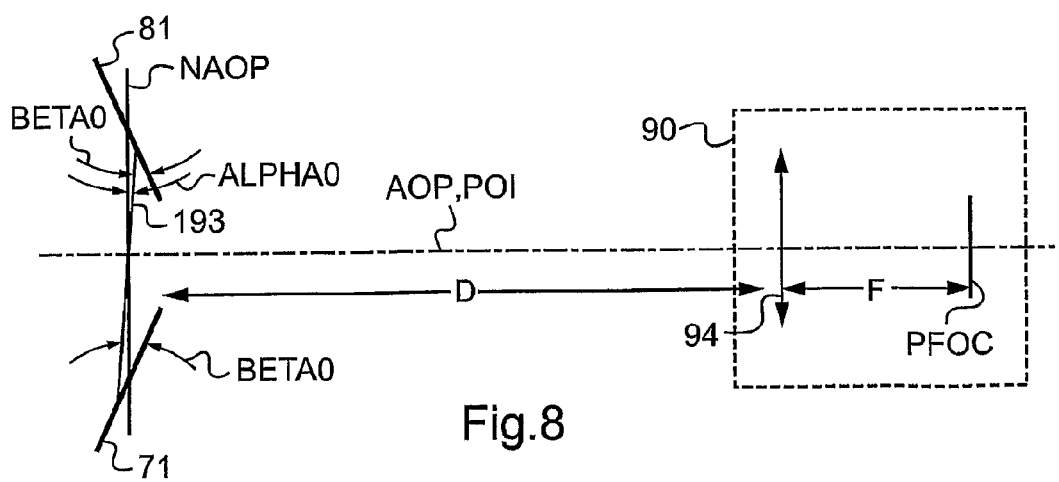
FIG. 8 is a diagrammatic plan view seen from above showing the position-identification system and the image capture means.

As shown diagrammatically in FIG. 8, the longitudinal direction of the geometrical pattern 193 of the holder bar 190 forms an angle ALPHA0 with the normal NAOP to the optical axis AOP when the determination device is viewed from above. Similarly, the longitudinal direction of each geometrical pattern 71, 81 of the corresponding position-identification elements 70, 80 forms an angle BETA0 with the longitudinal direction of the geometrical pattern 193 of the holder bar 190. It is also assumed that the geometrical patterns 71 and 81 are each of the same known length H and that the geometrical pattern 193 likewise possesses a known length L.

By measuring the spacing between the dark bands, the apparent length T of the geometrical pattern 193 of the holder bar 190 is measured in the focal plane PFOC of the objective lens 94. The following relationship applies:

$L*\cos(ALPHA0)*F/D=T$ where F is the focal length of the objective lens 94 and D is the distance between the image capture appliance 90 and the origin O of the frame of reference associated with the position-identification system 20.

The apparent lengths T1 and T2 of the geometrical patterns 71, 81 are measured in the focal plane PFOC. The following relationships are used:

$H*\cos(BETA0-ALPHA0)*F/D=T1$ and $H*\cos(BETA0+ALPHA0)*F/D=T2$

BETA0 is then calculated approximately by summing the two apparent lengths T1 and T2:

$T1+T2=2*\cos BETA0*\cos ALPHA0*H*F/D$ and by considering that cos ALPHA0 is close to 1, the following is obtained:

$T1+T2=2*\cos BETA0*H*T/L$

This gives an approximate value for BETA0.

Thereafter, the ratio K between these two lengths is calculated in order eliminate H*F/D:

$$K = \frac{\cos BETA0 \cos ALPHA0 + \sin BETA0 \sin ALPHA0}{\cos BETA0 \cos ALPHA0 - \sin BETA0 \sin ALPHA0}$$

Since the values of K and BETA0 are known, ALPHA0 is calculated using the following relationship:

$$\tan(ALPHA0) = \frac{(K-1)*\cos BETA0}{(K+1)*\sin BETA0}$$

The distance D is deduced therefrom using the measurement of T, given that the values of F and L are known:

$D=L*\cos(ALPHA0)*F/T$

It is also possible to use a laser diode telemeter to determine this separation distance directly.

The processor and calculation system 93 also measures the spacing between the dark bands of the geometrical pattern 81 of the horizontal position-identification element 80 in the image it has captured in the wearing configuration. As above, in order to limit measurement errors on the captured image due to the pixels of the captured image, the processor and calculation system 93 measures the differences between the bands in pairs and calculates the average of these differences. Thereafter, by comparison with a reference configuration of the geometrical pattern 81 for which the angle ARHG and the spacing between the bands are known, it determines the band spacing variation between the wearing configuration and the reference configuration. Band spacings are compared while taking account of the scale factor of the captured image. Thereafter, the processor and calculation system 93 determines the angle ARHG as a function of this spacing variation. The angle AMG is then determined from the angle ARHG.

As shown in FIG. 2, the angle ARV is defined as being the angle formed in projection onto the sagittal plane PSAG between firstly the frame vertical plane PVM and secondly the longitudinal direction of the geometrical pattern 61. When this angle ARV varies, the spacing between the dark bands also varies in projection onto the image capture plane PCI. This angle ARV is equal to the sum of the angle AMV plus the constant angle GAMMA of 30 degrees formed between the geometrical pattern 61 and the normal N90. The angle ARV thus varies in the same manner as the angle AMV.

The processor and calculation system 93 then measures the spacing between the bands of the geometrical pattern 61 in the image it has captured. As above, a reference configuration is provided of the geometrical pattern 61 for which the data pair constituted by the angle ARV and the spacing between the bands is known. By comparing the values of the band spacing measured on the captured image with the reference band spacing values, the processor and calculation system 93 deduces a spacing variation. As before, the band spacings are compared while taking account of the scale of the captured image. Thereafter, the processor and calculation system determines the angle ARV as a function of this spacing variation. The angle AMV is then determined from the angle ARV.

The processor and calculation system thus determines the orientation of the axes XLG and XLD of the left and right lenses respectively relative to the Frankfort plane and to the sagittal plane PSAG. Consequently, the orientations of the planes associated with the left and right presentation lenses are known in the frame of reference of the wearer. The orientation of each corrective lens for mounting in the frame relative to the corresponding eye is thus also known.

In a wearing configuration in which the wearer is looking straight ahead facing the image capture appliance 90, i.e. in which the sagittal plane PSAG is perpendicular to the image capture plane PCI, the angle AMG must be equal to the angle AMD.

When the angles AMG and AMD present a difference in value, it can be deduced that the wearer's head is turned through a posture angle APIV defined as follows.

As shown in FIG. 6, the posture angle APIV is the angle formed in the horizontal plane or Frankfort plane PF between the sagittal plane PSAG and the observation plane POI that contains the center 96 of the pupil 95 of the image capture appliance 90 and the vertical axis of rotation of the head ART.

The difference in value between the value AMG and the angle AMD is proportional to the value of the posture angle APIV. The processor and calculation system 93 then calculates a value for the posture angle APIV as a function of the value difference measured between the angles AMG and AMD. This value for the posture angle APIV serves to correct the values for the angles AMG and AMD.

In addition, to improve the personalization of the optical design of each lens, geometrico-morphological parameters are also determined that enable the distribution of index gradients to be improved while designing the lens. The processor and calculation system 93 thus uses image recognition, taking the scale factor into account, to recognize the width B and the length A of each of the rims 11, 12 surrounding the presentation lenses.

The processor and calculation system 93 also uses image recognition to determine the height HG, HD of each of the eyes OG, OD, this operation corresponding to measuring, in the captured image and while taking the scale factor into account, the distance between a separation line positioned over the center of each pupil PG, PD and the reference point taken as being the lowest point of the corresponding lens.

In order to measure the pupillary distance PDS, the processor and calculation system 93 uses image recognition on each eye to determine the center of the pupil (or of the iris). The segment defined by the centers obtained in this way of the two pupils PG and PD provides the pupillary distance PDS. It is also possible to measure the pupillary half-distances PDSD and PDSG by measuring the horizontal position of the center of each pupil PG, PD relative to the center of the nose bridge 15.

In this example, the pupillary distance PDS or the pupillary half-distances PDSD and PDSG are measured for a reference convergence configuration. In this reference convergence configuration, provision is made for the eyes of the wearer to fix on a light on the image capture means, e.g. the LED 92, at which the wearer gazes. The processor and calculation system then determines the value of this pupillary distance for vision at infinity as a function of the capture-taking distance and of the corresponding measured value for the pupillary distance PDS (or half-distance).

Naturally, all of the measurements performed on the image take the scale factor into account.

It is also possible to improve the accuracy with which values are calculated for the pupillary distance, the pupillary half-distance, and the width dimension A by correcting these calculated values as a function of the previously calculated angles AMD and AMG, and indeed of the posture angle APIV or of the distance difference between the eyes OD, OG and the corresponding lenses 100, 101. Likewise, measurements of the height dimension B and of the heights HG, HD of the pupils of each of the eyes can be improved by taking the value of the angle AMV into account.

The inclinations of the longitudinal directions of the geometrical patterns 71 and 81 relative to the longitudinal directions of the sticks 23 and 24 are used to increase the values of the band spacing variations when the angles AMG and AMD vary. The spacing between two bands that results from the variation in the angles AMG and AMD relative to the known reference configurations is thus more easily identifiable. Thus, the comparison of the spacings is representative of the horizontal component of the orientation of each of the rims 11, 12 of the frame, and thus of each of the lenses, thereby limiting measurement errors.

The same applies to the inclination of the longitudinal direction in the geometrical pattern 61 relative to the normal N90. This angle of inclination increases the values of the spacing variations between the bands when the angle AMV varies.

Determining the Distance between the Lens and the Center of the Corresponding Eye of the Wearer It is then desired to determine the distance in a horizontal direction of the sagittal plane PSAG, i.e. along the axis Z, between the lens 100 and the center CROD of the right eye OD, and also the distance along the same direction between the lens 101 and the center CROG of the left eye OG. This is done by applying the method of the present invention to determine the position along the Z axis of the center of rotation CROG or CROD constituting a remarkable point for the eye in the (O,X,Y,Z) frame of reference associated with the wearer's head and embodied by the position-identification system 20. Thereafter, while taking account of the now known configuration of the lens in question in the (O,X,Y,Z) frame of reference, the looked-for distance between the center of rotation of the eye and the lens is deduced.

During a first step S1, the image capture appliance 90 is placed facing the wearer's face so that the wearer's head presents a first posture relative to the entry pupil 95 of the image capture appliance 90.

This first relative posture is such that the image capture appliance observes the wearer generally in face view and not in profile view. Measuring the positions of the eyes from an image taken in face view offers several advantages, in comparison with an image taken in profile view. In practice, the operation of processing the image is more reliable insofar as the rims and the temples of the frame do not run risk of masking the eye, and insofar as the method of calculation that is explained below does not require the point of the rear face of the lens that faces the eye to be recognized (which operation is risky). Furthermore, one or more face views of the wearer enable other geometrico-morphological parameters of the wearer to be measured such as the pupillary distance and the height of the eyes, the curvature of the frame, the pantoscopic angle of each lens when worn (i.e. the angle between the general plane of the lens and the vertical), as mentioned above, or indeed the visual behavior of the wearer (in particular the wearer's tendency to move the eyes or the head to a greater or lesser extent when scrutinizing a field of view).

Below, the occurrences of the various defined geometrical elements such as straight lines, planes, and angles that correspond to this first posture are given the index 1. This applies in particular to the observation plane POI, which in this first occurrence is written POI1, to the sagittal plane PSAG, which in this first occurrence is written PSAG1, to the posture angle APIV, which in this first occurrence is written APIV1, and to the frame of reference (O,X,Y,Z) which in this first occurrence is written (O1,X1,Y1,Z1).

During a second step S2, a first plane image of the wearer's head is captured in this face view first relative posture by means of the image capture appliance 90 and as described above.

During a third step S3, the processor and calculation system 93 identifies in this first image the image of a first predetermined reference point of each eye.

Figure 9:
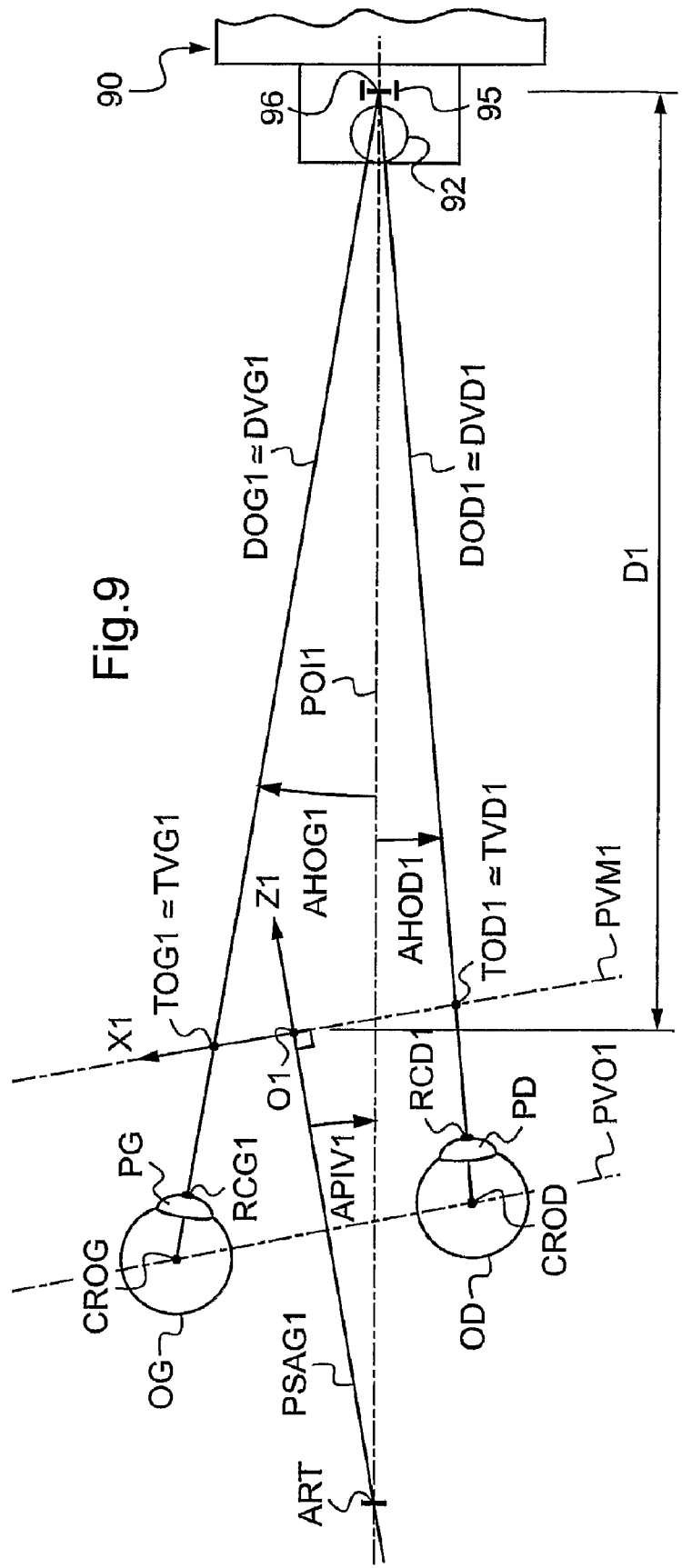
FIG. 9 is another diagrammatic plan view from above showing the position-identification system and the image capture means, in a first posture.
Figure 10:
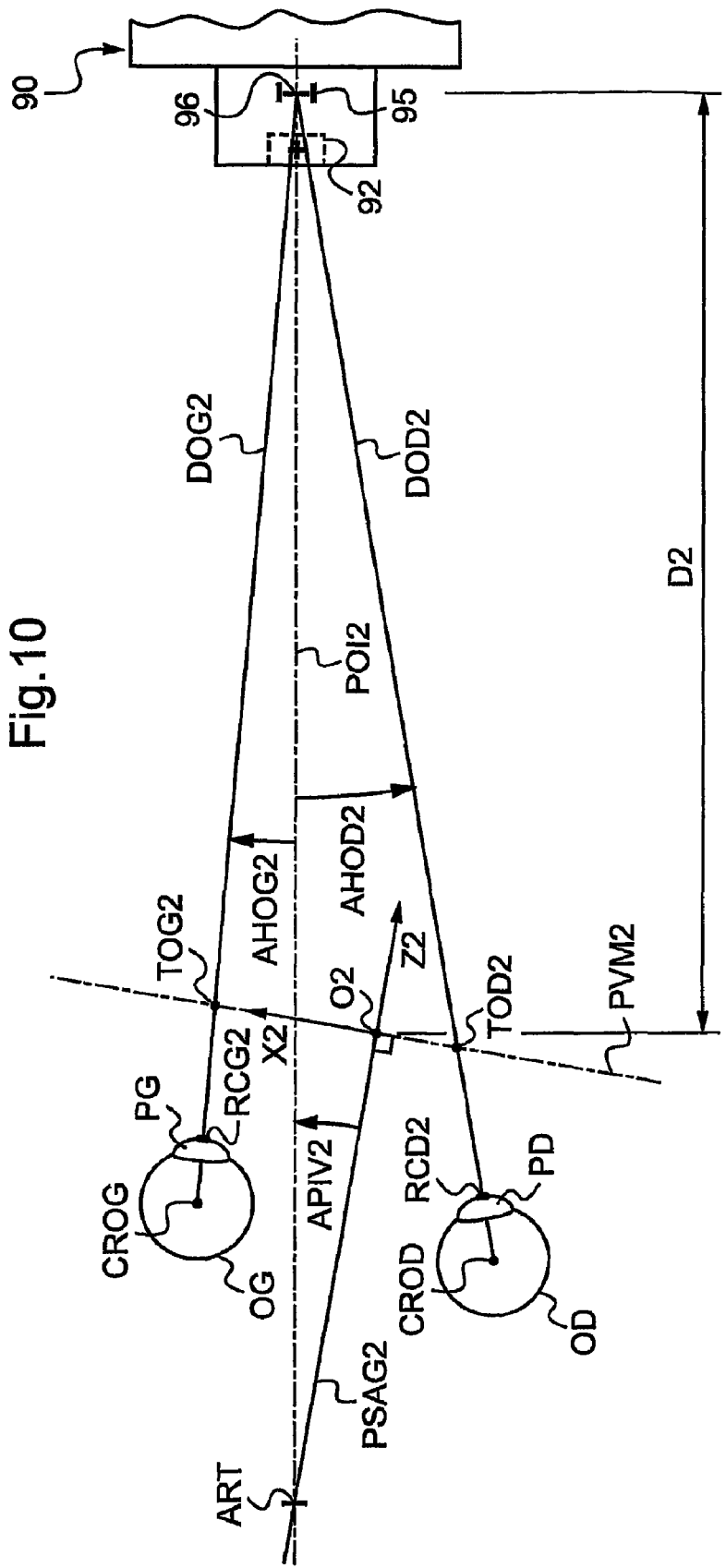
FIG. 10 is a view analogous to FIG. 9, but in a second posture.

In the example shown in FIGS. 9 and 10, this first reference point of the eye is the reflection RCG1, RCD1 of the visible light source constituted by the LED 92 as reflected on the cornea of the left eye OG and of the right eye OD, respectively.

The processor and calculation system 93 also calculates the configuration of the image capture appliance 90 in the first occurrence (O1,X1,Y1,Z1) of the frame of reference (O,X,Y,Z) associated with the wearer's head, from the first captured image of the position-identification system 20 in the first posture. In particular, it calculates a first value APIV1 for the posture angle APIV and the position of the center 96 of the entry pupil 95 of the image capture appliance 90. Typically, and as measured above, the processor and calculation system 93 calculates the first value APIV1 for the posture angle APIV as a function of the difference between the measured values AMG1 and AMD1 of the angles AMG and AMD in this first posture, while the distance between the origin O1 of the frame of reference and the center 96 of the pupil 95 is obtained by a scaling calculation deduced from the apparent magnitude of a geometrical pattern of the position-identification system 20 of real size that is known.

During a fourth step S4, the picture-taking angle is modified: the image capture appliance 90 is placed facing the wearer's face in such a manner that the wearer's head presents a second posture relative to the entry pupil 95 of the image capture appliance 90, which second posture is different from the first. As a result, the relative position the wearer's head relative to the image capture appliance is changed, either by moving the absolute position of the wearer's head, e.g. by asking or causing the wearer to turn the head about its vertical axis of rotation ART, either by moving the image capture appliance 90 relative to the wearer, or indeed by combining these two movements.

In particular, the relative position of the pupil of the image capture appliance and the vertical axis of rotation ART of the wearer's head remains identical during the two image captures, with the wearer following a visible light source forming a sighting point that causes the wearer's head to be turned about said vertical axis of rotation ART.

By way of example, it is considered that the relative positions of the pupil of the image capture appliance and the vertical axis of rotation ART of the wearer's head are identical in the first and second postures, providing the subject's head does not move transversely between said first and second postures by more than 20 percent of the distance that exists between the pupil of the image capture appliance and the vertical axis of rotation ART in the first posture, in a direction perpendicular to the optical axis of the image capture appliance.

For example, for a distance of 1 meter (m) between the pupil of the image capture appliance and the vertical axis of rotation ART in the first posture, a transverse displacement of 20 percent of said distance corresponds to a transverse displacement of 20 centimeters (cm) in a direction perpendicular to the optical axis of the image capture appliance, to one side or the other of said optical axis.

The subject preferably merely turns the head about the vertical axis of rotation ART while keeping the head straight, i.e. while maintaining a horizontal Frankfort plane. This turning of the subject's head about the vertical axis of rotation ART preferably presents an amplitude lying in the range 5 degrees to 60 degrees.

This modifies the posture angle APIV.

Like the first relative posture, this second posture is one in which the image capture appliance observes the wearer generally in face view and not in profile.

Below, the occurrences of the various defined geometrical elements such as straight lines, planes, and angles, that correspond to this second posture are given the index 2. This applies in particular to the observation plane POI which in this second occurrence is written POI2, to the sagittal plane PSAG, which in this second occurrence is written PSAG2, to the posture angle APIV, which in this second occurrence is written APIV2, and to the frame of reference (O,X,Y,Z), which in this second occurrence is written (O2,X2,Y2,Z2).

During a fifth step S5, a second plane image of each eye is captured in this second relative posture by means of the image capture appliance 90.

During a sixth step S6, the processor and calculation system 93 identifies, in this second image, the image of a second predetermined reference point for each eye. In the example shown in FIGS. 9 and 10, this second reference point of each eye is the reflection RCG2, RCD2 of the diode 92 as reflected on the cornea of the left eye OG and of the right eye OD, respectively. The first and second reference points of each eye in this example thus coincide, for the eye in question, at a single point that is approximately the center of the cornea or of the iris.

The processor and calculation system 93 calculates the configuration of the image capture appliance 90 in this occurrence (O2,X2,Y2,Z2) of the frame of reference (O,X,Y,Z) associated with the wearer's head on the basis of the second captured image of the position-identification system 20, as described above. In particular, it calculates a second value APIV2 for the posture angle APIV and for the position of the center 96 of the entry pupil 95 of the image capture appliance 90.

During a seventh step S7, the processor and calculation system 93 calculates, in the first relative posture and for each eye OD, OG respectively, a first observation straight line DOD1, DOG1 connecting the center 96 of the pupil of the image capture appliance 90 with the first reference point RCG1, RCD1 of the eye, and in the second relative posture, a second observation straight line DOD2, DOG2 connecting the center 96 of the pupil of the image capture appliance 90 and the second reference point RCG2, RCD2 of the eye.

During an eighth step S8, the processor and calculation system 93 performs a calculation to verify whether the first observation straight lines DOG1, DOD1 present, relative to the wearer's head, respective configurations that are substantially distinct from those of the second observation straight lines DOG2, DOD2. If not, the processor and calculation system 93 issues an error message or executes steps S1 to S3 or steps S4 to S6 again. If so, the processor and calculation system 93 proceeds to the following step S9.

Furthermore, the face view character of the second image, as mentioned above, can be quantified in the following manner. The first relative posture is such that each of these first observation straight lines DOD1, DOG1 forms a respective angle of less than 45 degrees with its projections onto the sagittal plane PSAG1 and onto the Frankfort plane PF of the wearer. Similarly, the second relative posture is such that each of these second observation straight lines DOD2, DOG2 forms a respective angle of less than 45 degrees with its projections onto the sagittal plane PSAG2 and onto the Frankfort plane PF.

The processor and calculation system 93 verifies compliance with this criterion. If the criterion is not satisfied, the processor and calculation system 93 issues an error message and the first relative posture and/or the second relative posture is/are modified prior to capturing a new first image. If the criterion is satisfied, then the method moves on to the following step.

During a ninth step S9, the processor and calculation system 93 calculates the position of the center of rotation CROG, CROD of each eye OG, OD as a function of the images of the first and second reference points of the eye in question and of the first and second values APIV1, APIV2 for the posture angle APIV.

Thereafter, the processor and calculation system 93 compares the images of the first and second reference points of each eye to deduce therefrom the apparent angular movement of the eye as seen between the two different viewpoints corresponding to the first and second relative postures. Given the information concerning the two viewpoints constituted by the first and second values APIV1 and APIV2 for the posture angle APIV, a parallax calculation then makes it possible to obtain the looked-for positions of the centers CROG, CROD of the eyes along the axis Z.

In order to calculate the position of the center of rotation CROG, CROD of each eye, the processor and calculation system 93 uses the image of the first reference point of the eye in question and the first value for the posture angle APIV1 to calculate the coordinates in said frame of reference (O,X,Y,Z) of the wearer's head for the first observation straight line DOD1, DOG1 connecting the center 96 of the entry pupil 95 of the image capture appliance 90 with the first reference point of each eye OD, OG. Likewise, the processor and calculation system 93 uses the image of the second reference point of the eye and the second value for the posture angle APIV2 to calculate the coordinates in said frame of reference (O,X,Y,Z) of the wearer's head for the second observation straight line DOD2, DOG2 connecting the center of the pupil of the image capture appliance with the second reference point of each eye.

The processor and calculation system 93 then calculates the position of the center of rotation of each eye CROG, CROD in the frame of reference (O,X,Y,Z) as a function of the coordinates of the first and second observation straight lines DOG1, DOD1, DOG2, DOD2. The position of the center of rotation CROG of the left eye is calculated as being the position of the point of intersection of these straight lines, or if they do not intersect exactly, the position of the point where these observation straight lines DOG1, DOG2 come closest together. Similarly, the position of the center of rotation CROD of the right eye is calculated as the point of intersection between the straight lines, or if they do not intersect exactly, as the position where the two observation straight lines DOD1 and DOD2 come closest together.

The wearer's viewing direction is taken into consideration. While the first and second images are being captured, the eye is looking at the LED 92 which attracts the wearer's gaze. In each of the first and second relative postures, the center of the diode 92 corresponds respectively to first and second sighting points. The positions of these sighting points are therefore known in the frame of reference of the image capture appliance 90. Specifically, the sighting points are situated in the observation plane POI close to the pupil of the image capture appliance.

The positions of the centers of rotation CROD and CROG of the eyes are then calculated also as a function of the sighting points embodied by the diode 92 in these two positions.

In the first relative posture, two sighting straight lines DVD1 and DVG1 are defined that connect the reference points RCD1 and RCG1 respectively to the sighting point, i.e. to the LED 92 in the first posture. Similarly, in the second relative posture, two first sighting straight lines DVD2 and DVG2 are defined respectively connecting the reference points RCD2 and RCG2 to the sighting points, i.e. to the LED 92 in the second posture.

Since, in the example shown in FIGS. 9 and 10, the LED 92 is situated close to the entry pupil 95 of the image capture appliance 90, it can be assumed that in order to calculate the positions of the centers CROG and CROD in the frame of reference (O,X,Y,Z) that both eyes OD and OG look substantially towards the entry pupil of the image capture appliance 90 in each of the first and second postures. As a result, in the third posture, the sighting straight lines DVG1 and DVD1 coincide respectively with the observation straight lines DOG1 and DOD1, and similarly, in the second posture, the sighting straight lines DVG2 and DVD2 coincide respectively with the observation straight lines DOG2 and DOD2. This approximation serves to take account, in this example, of the position of sighting point in each of the first and second relative postures.

Left and right horizontal observation angles AHOG and AHOD are then defined as formed respectively between the left and right observation lines DOG and DOD with their respective projections onto the observation plane POI. The occurrences of these angles in the first and second postures, respectively written AHOG1, AHOD1, AHOG2, and AHOD2 are calculated by the processor and calculation system 93. For this purpose, the processor and calculation system 93 acts for each posture to calculate the position of the observation plane POI as a function of the corresponding first and second captured images of the position-identification system 20, and it determines the apparent angles with which the reference points were seen, i.e. specifically the corneal reflections RCG1, RCD1, RCG2, and RCD2 of the image capture appliance 90 in the first and second relative postures. If, as is usually true, the observation plane POI coincides approximately with the optical axis AOP of the image capture appliance 90, then the looked-for angles AHOG and AHOD are equal to the observed apparent angles. Otherwise, the appropriate correction is applied to the apparent angles to deduce therefrom the looked-for angles AHOG and AHOD.

On the basis of the values calculated in this way for these angles, the processor and calculation system 93 acts for each posture to calculate the respective traces TOG and TOD of the observation straight lines DOG and DOD on the frame vertical plane PVM. These traces are naturally points that are written TOG1 and TOD1 for the first posture and TOG2 and TOD2 for the second posture.

The respective traces TVG and TVD are also defined for the sighting straight lines DVG and DVD on the frame vertical plane PVM. Since the wearer is looking specifically towards the pupil of the image capture appliance, these points TVG and TVD coincide approximately with the points TOG and TOD in both the first and the second postures. More precisely, the processor and calculation system 93 calculates the respective abscissas X(TOG1) and X(TOD1) of the points TOG1 and TOD1 relative to the X axis in the first occurrence (O1,X1,Y1,Z1) of the frame of reference (O,X,Y,Z) and the respective abscissas X(TOG2) and X(TOD2) of the points TOG2 and TOD2 in the second occurrence (O2,X2,Y2,Z2) of the frame of reference (O,X,Y,Z). It can then deduce therefrom the looked-for distances between the frame vertical plane PVM and the centers of rotation CROG and CROD of the left and right eyes, which distances correspond to the additive inverses of the abscissas along the axis Z, written respectively Z(CROG) and Z(CROD) for the centers CROG and CROD. The following formulae can be applied:

$$Z(CROD) = -\text{Abs}\left(\frac{X(TOD1) - X(TOD2)}{\tan(AHOD1 + APIV1) - \tan(AHOD2 + APIV2)}\right)$$

$$Z(CROG) = -\text{Abs}\left(\frac{X(TOG1) - X(TOG2)}{\tan(AHOG1 + APIV1) - \tan(AHOG2 + APIV2)}\right)$$

where "Abs" is the absolute value function and "tan" is the tangent function.

Figure 11:
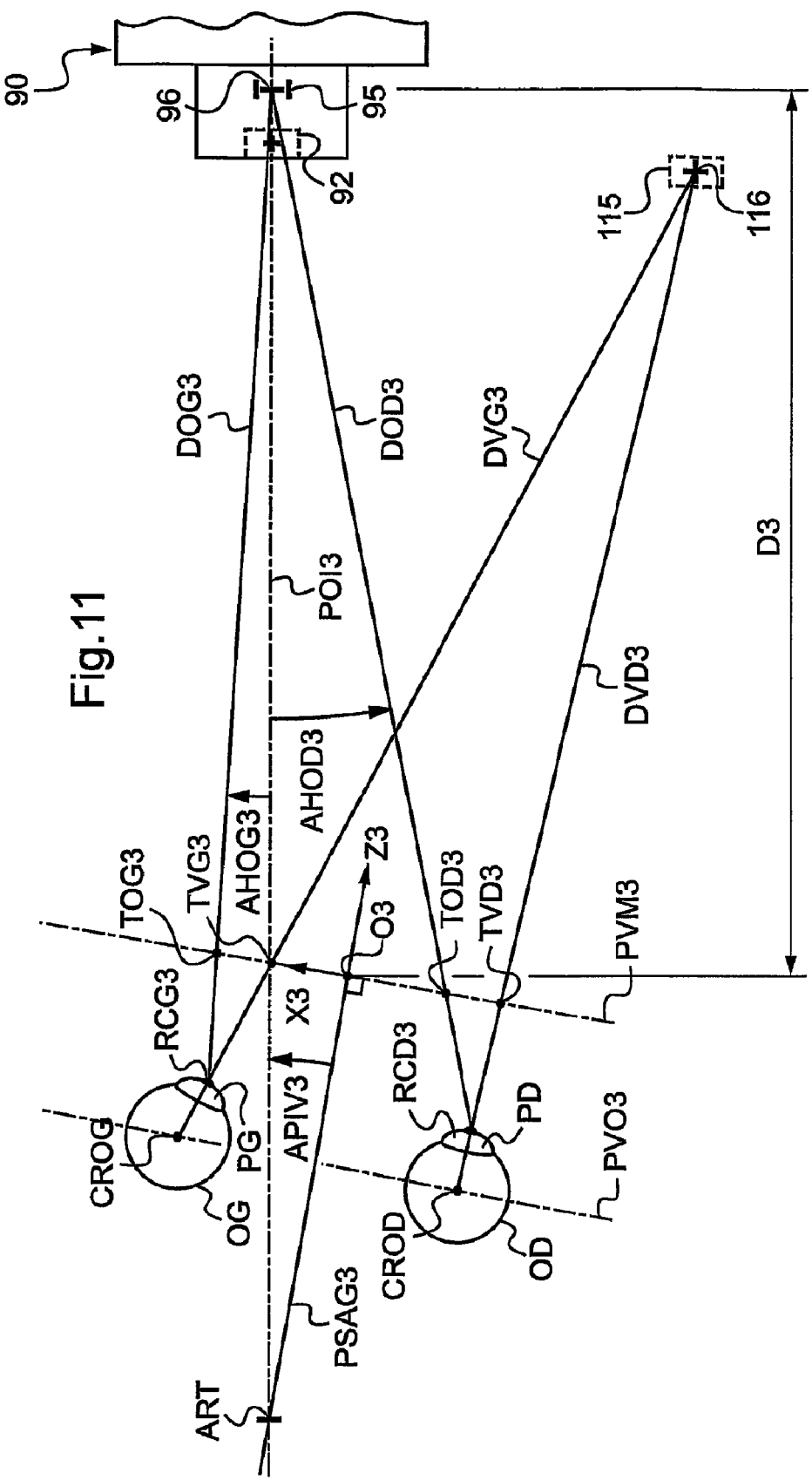
FIG. 11 is a view analogous to FIG. 10 but in a third posture, with an additional visible light source forming a known sighting point for the wearer.

FIG. 11 shows a variant implementation of the invention, which implementation may be advantageous for gaining accuracy or for capturing images for viewing directions that correspond to far and near vision, or indeed for improving eye radius calculation.

In this example, the device includes a second visible light source 115 such as an LED, having a center 116 that constitutes a sighting point for attracting the gaze of the wearer. The method essentially reproduces all of the steps as described above. Below, the description relates only to the additions or modifications involved compared with the implementation described above in detail.

During a tenth step S10, a third relative posture (O3,X3, Y3,Z3) of the subject's head is provided relative to the entry pupil 95 of the image capture appliance 90. This third posture is identical to or distinct from the first and second relative postures.

FIG. 11 shows a third relative posture that takes the place of or replaces the first relative posture or the second relative posture, and in which a third image of the wearer's face and of the position-identification system 20 is captured.

In the first and second postures shown in FIGS. 9 and 10, the reference points taken into account for calculating parallax are the corneal reflections of the LED 92 that is situated close to the entry pupil of the image capture appliance 90. In the third posture shown in FIG. 11, provision is made for the wearer to look towards the LED 115 at a position relative to the pupil 95 of the image capture appliance 90 that is known and entered as a parameter into the memory of the processor and calculation system 93. Relative to the frame of reference (O,X,Y,Z) associated with the head of the subject, the position of the LED 115 is different than the position of the LED 92.

In an eleventh step S11, the image capture appliance 90 captures a third plane image in face view of the subject's head together with the position-identification system 20 and the eyes while in this third relative position.

The position-identification system 93 calculates a third value APIV3 for the posture angle from this third captured image.

In a twelfth step S12, the processor and calculation system 93 identifies the image of a third predetermined reference point for each eye in this third image. In this example, this reference point is the reflection RCG3, RCD3 of the LED 115 reflected respectively by the cornea of the left eye and of the right eye. This applies because both eyes are looking at the LED 115.

Then, during a thirteenth step S13, the processor and calculation system 93 calculates the radius ROG, ROD of each eye as a function:
- of the images of the corneal reflections RCG1, RCD1 of the first image and/or of the corneal reflections RCG2, RCD2 of the second image, and also the images of the corneal reflections RCG3, RCD3 of the third image;
- of the first and/or second value APIV1, APIV2 and of the third value APIV3 for the posture parameter APIV; and
- of the known positions of the sighting points 92 and 116 relative to the pupil 95 of the image capture appliance 90.

The group of steps S10, S11, S12 is specifically distinct from the group of steps S1, S2, S3 and also from the group of steps S4, S5, S6. In a variant, provision could be made for the steps S10, S11, S12 to coincide with one or other of the groups of steps S1, S2, S3 and S4, S5, S6. Thus, using only two images captured in face view, both the position of each eye relative to the lens and the radius of each eye are thus calculated in combination.

The processor and calculation system 93 then acts on the image of the third reference point RCG3, RCD3 (corneal reflection of the LED 115) of the eye in question and the third value of the posture angle APIV3 to calculate the coordinates in the frame of reference (O,X,Y,Z) of the wearer's head for a third observation straight line DOD3, DOG3 connecting the center 96 of the entry pupil 95 of the image capture appliance 90 with the third reference point RCG3, RCD3 (corneal reflection of the LED 115) of the eye OD, OG.

The observation direction of the wearer is taken into consideration.

When capturing the first and second images, each eye looks at the LED 92. However, in the third configuration shown in FIG. 11, each eye is looking at the LED 115 that is at a distance from the image capture appliance. The center 116 of the diode 115 constitutes a third sighting point of position that is known in the frame of reference of the image capture appliance 90. The positions of the centers of rotations CROD, CROG of the eyes are then calculated in addition as a function of the positions of the sighting points embodied by the LED 92 in both postures.

Two third sighting straight lines DVD3 and DVG3 respectively connecting the third reference points constituted by the corneal reflections RCD3 and RCG3 of the sighting points, i.e. the center 116 of the LED 115 are then defined in the third relative posture.

Since the LED 115 is situated at a distance from the entry pupil 95 of the image capture appliance 90, the third aiming straight lines DVG3 and DVD3 are clearly distinct from the third observation straight lines DOG3 and DOD3. It is therefore necessary, when calculating the positions of the centers of rotation of the eyes, specifically to take account of the position of the third aiming point as constituted by the LED 115.

The third occurrences AHOG3 and AHOD3 of the angles AHOG and AHOD (defined above) in the third posture are calculated by the processor and calculation system 93, as described above for the first and second postures.

From the values for these angles, the processor and calculation system 93 calculates the respective traces TOG3 and TOD3 of the third occurrences of the observation straight lines DOG3 and DOD3 in the third occurrence of the frame vertical plane PVM3, and also the respective traces TVG3 and TVD3 of the third occurrences of the sighting straight lines DVG3 and DVD3 in the third occurrence of the frame vertical plane PVM3. More precisely, the processor and calculation system 93 calculates the respective abscissas X(TOG3) and X(TOD3) of the points TOG3 and TOD3 along the X axis in the third occurrence (O3,X3,Y3,Z3) of the frame of reference (O,X,Y,Z), and also the respective abscissas X(TVG3) and X(TVD3) of the points TVG3 and TVD3 in the third occurrence (O3,X3,Y3,Z3) of the frame of reference (O,X,Y,Z). It can then deduce the looked-for distances between the frame vertical plane PVM and each of the centers of rotation CROG and CROD of the left and right eyes, which distances correspond to the additive inverses of the abscissas along the Z axis of the centers CROG and CROD, and written respectively Z(CROG) and Z(CROD).

The processor and calculation system 93 also calculates the radius of the eye by taking advantage of the fact that between third posture and the first and second postures, the angular position of each eye about its center of rotation CROG, CROD has changed relative to the entry pupil 95 of the image capture appliance 90.

The processor and calculation system 93 calculates the radius of each eye OD, OG from:
  the respective abscissas X(TVG3), X(TVD3), X(TOG3), X(TOD3) of the points TVG3, TVD3; TOG3, TOD3 in the third occurrence (O3,X3,Y3,Z3) of the frame of reference (O,X,Y,Z); and
  the respective abscissas X(TOG1), X(TOD1) of the points TOG1, TOD1 in the first occurrence (O1,X1,Y1,Z1) of the frame of reference (O,X,Y,Z) (the points TVG1, TVD1 respectively coinciding with the points TOG1, TOD1); and/or
  the respective abscissas X(TOG2), X(TOD2) of the points TOG2, TOD2 in the second occurrence (O2,X2,Y2,Z2) of the frame of reference (O,X,Y,Z).

Thus, for example, if three images are captured respectively in the first, second, and third postures, with the second and third occurrences corresponding to the posture angles APIV2 and APIV3 being equal, and the second and third occurrences D2 and D3 of the distance D between the image capture appliance 90 and the origin O of the frame of reference (O,X,Y,Z) associated with the wearer's head being equal or nearly equal, it is possible to make use of the second and third captured images to perform a simple and accurate calculation of the radius of each eye. If the radii of the left and right eyes are written respectively ROG and ROD, the processor and calculation system 93 can execute the following formulae:

$$ROG = \mathrm{Abs}\left(\frac{X(RCG2) - X(RCG3)}{\mathrm{OMEGA}}\right)$$

$$ROD = \mathrm{Abs}\left(\frac{X(RCD2) - X(RCD3)}{\mathrm{OMEGA}}\right)$$

$$\mathrm{OMEGA} = \arctan\left(\frac{d(ART, PVO) \cdot \sin(APIV2)}{d(ART, PVO) \cdot (1 - \cos(APIV2)) + D2}\right) + \arctan\left(\frac{\mathrm{Abs}(X96 - X116) - d(ART, PVO) \cdot \sin(APIV2)}{d(ART, PVO) + D2 - d(ART, PVO) \cdot \cos(APIV2)}\right)$$

where:
  X(RCG2), X(RCD2) are respectively the abscissas along the X axis of the frame of reference (O,X,Y,Z) of the left and right corneal reflections RCG and RCD in the second posture;
  X(RCG3), X(RCD3) are respectively the abscissas along the X axis of the frame of reference (O,X,Y,Z) of the left and right corneal reflections RCG and RCD in the third posture;
  X96 and X116 are respectively the abscissas along the X axis of the sighting points 96 and 116; and
  d(ART,PVO) is the distance between the vertical axis of rotation ART of the head and the frame vertical plane PVO.

To terminate, the processor and calculation system 93 deduces the configuration relative to the eyes of the wearer of the frame of reference of the corrective lens that is to be made from the distance between each lens 100, 101 and the corresponding eye OD, OG and from the orientation of each lens.

Other Variants

The present invention is not limited in any way to the embodiments described and shown, and the person skilled in the art can apply any variant within the spirit of the invention.

For example, it is possible to envisage measuring the position of the center of rotation CRO of the wearer's eye using an infrared light source close to or coinciding with the visible light source forming the sighting point for the wearer's gaze. Taking measurements in the infrared serves to increase the contrast of the pupil of the eye and of the corneal reflection in the captured images, thereby ensuring better measurement accuracy.

It is also possible to envisage calculating the mean position of the CRO of the wearer's eye by averaging the measurements for the position of the CRO of the wearer's eye in a plurality of captured images. The use of a known mathematical method such as the least squares method then serves to minimize errors in measuring this position.

In particular, using a method analogous to that described above, it is possible to measure the position of a remarkable point of each eye other than the center of rotation of said eye, such as, for example, the center of the pupil or of the iris, a point on the sclera that is adjacent to the canthus (corner of the eyelid) or to the top or bottom edge of an eyelid.

Furthermore, in the example shown in FIGS. 9 and 10, the first and second sighting points (in the first and second postures) are distinct since the first and second postures are distinct. Nevertheless, provision could be made for the first and second sighting points to coincide, with the observer observing in both the first and the second postures a single sighting point such as, for example, the center of an optionally light-emitting target fastened on a wall or resting on a table or a stand.

Advantageously, provision could also be made for at least two postures and sighting points to be such that when capturing an image in one of the postures, the gaze directions of the eyes correspond to far vision, and when capturing the image in another posture, the gaze directions of the eyes correspond to near vision. It is thus possible on the basis of images captured in this way to obtain additional data such as the pupillary distances and the heights of the eyes in far vision and in near vision, or indeed to obtain information concerning the behavior of the wearer (e.g. a tendency to move the eyes or the head to a greater or lesser extent on going from far vision to near vision, or vice versa).

Provision can also be made for the various postures of the wearer's head relative to the image capture appliance to be predetermined. The position of the image capture appliance is then stationary, or in any event predefined for each image capture, and the wearer is caused, for each image capture, to place the head in a desired and predefined posture, with the help of any suitable accessory for providing assistance in positioning. By way of example, such an accessory may be constituted by a laser pointer or aimer fitted to the frame or the position-identification system and associated with a target of known position to which the wearer is requested to point, or indeed a headrest device that holds the wearer's head stationary in a predefined posture. Under such circumstances, the acquisition of the various values for the posture parameter (such as the angle APIV) is global in the sense that the various postures used for measurement purposes are common to all wearers and the corresponding posture parameters are thus global parameters (or "global variables" in computer language) that are not acquired again for each measurement.

Provision can also be made for the device and the method to be designed to operate for an orientation of the Frankfort plane that is not parallel to the horizontal plane PH of the terrestrial frame of reference. It is also possible to implement the above-described method, but while assuming that the vertical direction is defined relative to the wearer and not relative to the terrestrial frame of reference. In other words, the vertical direction is then defined as being the direction perpendicular to the primary gaze axis of the wearer and contained in the sagittal plane PSAG. The horizontal plane, i.e. the plane perpendicular to the vertical direction, is then defined as coinciding with the Frankfort plane.

The method may also be applied with a pair of eyeglasses of the pierced type. Under such circumstances, each stick is fastened directly onto the corresponding presentation lens. The calculations or measurements performed relating to the rims (shape, orientation) in the above description are then performed relative to the presentation lenses mounted on the pierced type frame.

In a variant, for a rimmed type frame, provision can be made to implement the method with a rimmed frame that does not have presentation lenses. Under such circumstances, the rods carrying the bearing beads themselves bear against the rims of the frame. It is then possible to define overall for each rim its mean plane containing the position of the mounting cross. The above-described method is then performed to discover the orientation of that plane.

Still with a rimmed type frame, it is possible to provide for only a left or a right presentation lens, assuming that the configuration of the frame of reference for the other lens is obtained by symmetry relative to the plane of symmetry of the frame. Under such circumstances, it is possible to retain both position-identification elements associated with the two eyes so as to determine a pivot angle, if any. It is also possible to provide only one position-identification element associated with only one of the two eyes, assuming that the head is indeed straight and the plane of symmetry of the frame does indeed coincide with the sagittal plane.

It is also possible to envisage that the wearer does not keep the head straight in both the first and second relative postures. The wearer then turns the head about an axis that is perpendicular to the sagittal plane PSAG. The posture parameters that need determining then include an angle of rotation about said horizontal axis corresponding to an angle between the image capture appliance and the head of the subject in a vertical plane.

Finally, the order in which the steps are performed is not limiting and the person skilled in the art knows how to modify them at will while preserving overall coherence for the method.

The invention claimed is:

1. A method of measuring a position, in a horizontal direction of the sagittal plane (PSAG), of a remarkable point (CROD, CROG) of an eye (OD, OG) of a subject in a frame of reference (O,X,Y,Z) associated with the head of said subject, the method comprising the steps of:
    S1) arranging the subject's head in a first relative posture (O1,X1,Y1,Z1) relative to the entry pupil (95) of a single image capture appliance (90) placed facing the subject's face;
    S2) in said first relative posture, using the single image capture appliance (90) to capture, at a first point in time, a first plane image of the eye;
    S3) in said first image, identifying the image of a first predetermined reference point (RCG1, RCD1) of the eye;
    S4) arranging the subject's head in a second relative posture (O2,X2,Y2,Z2) relative to the entry pupil (95) of the image capture appliance (90), the second relative posture being distinct from the first relative posture (O1,X1,Y1,Z1);
    S5) in the second relative posture, using the single image capture appliance (90) to capture, at a second point in time, a second plane image of the eye, the first and second points in time being different;
    S6) in said second image, identifying the image of a second predetermined reference point (RCG2, RCD2) of the eye; and
    S9) calculating said position of the remarkable point (CROD, CROG) of the eye as a function exclusively of the first and second plane images of the first and second reference points (RCG1, RCD1, RCG2, RCD2) of the eye provided by said single image capture appliance (90), and of first and second values (APIV1, APIV2) of a posture parameter (APIV) associated respectively with the first and second relative postures,
    wherein said values of the posture parameter (APIV) are calculated using the following steps:
        placing a position-identification element (60, 70, 80; 700; 800) on the head of the subject, said element having at least one known geometrical characteristic;
        for each of the first and second plane images captured in each relative posture by means of the image capture appliance incorporating a plane image of the position-identification element (60, 70, 80; 700; 800), processing said image to measure a geometrical characteristic depending on the known geometrical characteristic of the position-identification element; and
        calculating the different values of the posture parameter (APIV) for the different postures as a function of said measured geometrical characteristic of the captured image of the position-identification element and of the known geometrical characteristic of the position-identification element.

2. A method according to claim 1, wherein, a first observation straight line (DOG1, DOD1) connecting the pupil (95) of the image capture appliance (90) and the first reference point (RCG1, RCD1) of the eye being defined in the first relative posture and a second observation straight line (DOG2, DOD2) connecting the pupil (95) of the image capture appliance (90) and the second reference point (RCG2, RCD2) of the eye being defined in the second relative posture, the first and second relative postures are such that these first and second observation straight lines form respective angles of less than 45 degrees relative to their projections onto the sagittal plane (PSAG) and onto the Frankfort plane (PF) of the subject.

3. A method according to claim 2, wherein, a first observation straight line (DOG1, DOD1) connecting the pupil (95) of the image capture appliance (90) and the first reference point (RCG1, RCD1) of the eye being defined in the first relative posture and a second observation straight line (DOG2, DOD2) connecting the pupil (95) of the image capture appliance (90) and the second reference point (RCG2, RCD2) of the eye are defined in the second relative posture, the first and second relative postures are such that these first and second observation straight lines present mutual distinct configurations relative to the subject's head.

4. A method according to claim 1, further including the steps of:
S7) calculating, in the first relative posture (O1,X1,Y1,Z1), a first observation straight line (DOG1, DOD1) connecting the pupil (95) of the image capture appliance (90) and the first reference point (RCG1, RCD1) of the eye, and in the second reference posture, a second observation straight line (DOG2, DOD2) connecting the pupil (95) of the image capture appliance (90) and the second reference point (RCG2, RCD2) of the eye; and
S8) verifying whether the first and second observation straight lines (DOG1, DOD1, DOG2, DOD2) present configurations that are substantially distinct from each other relative to the subject's head, and if not, executing steps S1 to S3 or S4 to S6 again.

5. A method according to claim 1, wherein the remarkable point of position that is looked-for is the center of rotation (CROD, CROG) of the subject's eye.

6. A method according to claim 5, wherein, at least while capturing the first and second images, the eye looks respectively at a first or second sighting point (92) having a known position relative to the pupil of the image capture appliance (90), and wherein, the following steps are executed:
S10) arranging the subject's head in a third relative posture (O3,X3,Y3,Z3) relative to the entry pupil (95) of the image capture appliance (90), which third relative posture is identical to or distinct from the first and second relative postures, the eye in said third relative posture looking at a third sighting point (116) having a position that is known relative to the pupil (95) of the image capture appliance (90) and that, relative to the frame of reference associated with the subject's head (O,X,Y,Z) is distinct from the position of the first or second sighting point (92);
S11) in said third relative posture (O3,X3,Y3,Z3), capturing a third plane image of the eye by means of the image capture appliance (90);
S12) identifying in said third image, the image of a third predetermined reference point (RCG2, RCD3) of the eye; and
S13) calculating the radius (ROG, ROD) of the eye as a function:
of the images of the first or second reference points (RCG1, RCD1, RCG2, RCD2) and of the third reference point (RCG3, RCD3) of the eye;
of the first or second value (APIV1, APIV2) of the posture parameter and a third value (APIV3) of the posture parameter (APIV) associated with the third posture; and
of the known positions of the sighting points (92, 116) relative to the pupil (95) of the image capture appliance (90);
the group of steps S10), S11), S12) being either distinct from both of the groups of steps S1), S2), S3) and S4), S5), S6), or else coinciding with one of said groups of steps.

7. A method according to claim 5, wherein, while capturing the first and second images, the eye looks respectively at first and second sighting points (92, 92; 92, 116) having positions that are known relative to each other, wherein the position of the center of rotation (CROD, CROG) of the subject's eye in the frame of reference associated with the subject is calculated also as a function of the relative positions of the sighting points (92, 92; 92, 116), and wherein the first and second postures and the first and second sighting points are such that, when capturing the first and second images, the corresponding directions of the gaze of the eye are distinct in the frame of reference associated with the subject's head (O,X,Y,Z).

8. A method according to claim 7, wherein at least two postures and two sighting points are such that while the image is being captured in one of the postures, the gaze directions of the eyes correspond to far vision, and while the image is being captured in another posture, the gaze directions of the eyes correspond to near vision.

9. A method according to claim 7, wherein the positions of the first and second sighting points (92, 116) relative to the pupil (95) of the image capture appliance (90) are distinct.

10. A method according to claim 9, wherein, in steps S1) and S4), the subject's head is arranged relative to the entry pupil of the image capture appliance (90) in the first and second relative postures in such a manner that the position of the pupil (95) of the image capture appliance (90) relative to a vertical axis of rotation (ART) of the subject's head is not modified between said first and second postures by a transverse movement of more than 200 millimeters in a direction perpendicular to the optical axis of the image capture appliance, and in such a manner that the subject pivots the head about said vertical axis of rotation through at least 5 degrees and not more than 60 degrees between said first and second postures in order to gaze respectively at the first and second sighting points that have different positions that are known relative to each other.

11. A method according to claim 7, wherein the positions of the first and second sighting points (92) relative to the pupil (95) of the image capture appliance (90) coincide.

12. A method according to claim 7, wherein,
the first reference point (RCG1, RCD1) of the eye is the reflection of a first light source (92) on the cornea of the eye, said first light source having a first position that is known relative to the entry pupil (95) of the image capture appliance (90);
the second reference point (RCG2, RCD2) of the eye is the reflection of a second light source (116) on the cornea of the eye, said second light source being distinct from or coinciding with the first light source and having a position that is known relative to the entry pupil (95) of the image capture appliance (90); and the position of the remarkable point (CROD, CROG) of the eye is calculated as a function, also, of the positions of the first and second light sources (92, 116), and wherein while capturing the first and second images, the eye looks respectively at the first and at the second light sources (92, 116), thereby constituting said first and second sighting points.

13. A method according to claim 1, wherein:

the first reference point (RCG1, RCD1) of the eye, in the first plane image, includes a reflection of a first light source (92) on the cornea of the eye, said first light source having a first position that is known relative to the entry pupil (95) of the image capture appliance (90);

the second reference point (RCG2, RCD2) of the eye, in the second plane image, includes a reflection of a second light source (116) on the cornea of the eye, said second light source being distinct from or coinciding with the first light source and having a position that is known relative to the entry pupil (95) of the image capture appliance (90); and the position of the remarkable point (CROD, CROG) of the eye is calculated as a function, also, of the positions of the first and second light sources (92, 116) and positions of the reflections of the first and second light sources on the cornea as recorded in the first and second images.

14. A method according to claim 1, wherein, in order to calculate the position of the remarkable point (CROD, CROG) of the eye in step S9), the following substeps are executed:

from the image of the first reference point (RCG1, RCD1) of the eye in the first plane image and from the first value (PSAG1) of the posture parameter, deducing coordinates, in said frame of reference associated with the head of said subject (O,X,Y,Z), of a first observation straight line (DOG1, DOD1) connecting the pupil (95) of the image capture appliance (90) and the first reference point (RCG1, RCD1) of the eye;

from the image of the second reference point (RCG2, RCD2) of the eye in the second plane image and from the second value (PSAG2) of the posture parameter, deducing the coordinates in said frame of reference of the subject's head, of a second observation straight line (DOD2, DOG2) connecting the pupil (95) of the image capture appliance and the second reference point of the eye (RCG2, RCD2); and calculating the position of the remarkable point of the subject's eye in the frame of reference associated with the subject's head as a function of the coordinates of the first and second observation straight lines (DOG1, DOD1, DOD2, DOG2).

15. A method according to claim 14, wherein the remarkable point of position that is looked for is the center of rotation (CROG, CROD) of the subject's eye, and wherein the position of said center of rotation (CROG, CROD) of the subject's eye is calculated as the position of one of i) a point of intersection of the two observation straight lines (DOG1, DOD1, DOD2, DOG2), and ii) when said two observation straight lines do not intersect, a point where said two observation straight lines come closest together.

16. A method according to claim 1, wherein said at least one posture parameter includes one or more of the following parameters:

the horizontal angle between the image capture appliance and the subject's head;

the vertical angle between the image capture appliance and the subject's head; and the distance between the image capture appliance and the subject's head.

17. A method according to claim 1, wherein the first and second reference points of the eye coincide at a single point of said eye, being one of the following points of the eye:

the center of the pupil or of the iris; and a point of the sclera adjacent to the canthus or to the upper or lower edge of the eyelid.

18. A method according to claim 1, wherein the first and second reference points of the eye are points of said eye that are distinct from each other.

19. A method according to claim 1, wherein the remarkable point of position that is looked-for consists in one of the following points of the eye:

the center of the pupil or of the iris; and a point of the sclera adjacent to the canthus or to the upper or lower edge of the eyelid.

20. A method according to claim 19, wherein the first and second reference points of the eye coincide with the remarkable point of said eye of position that is looked-for.

21. A method according to claim 1, wherein while capturing at least one of the images, the subject is fitted with an eyeglass frame having mounted thereon the position-identification element (60, 70, 80; 700; 800), and wherein, as a function of said measured geometrical characteristic of the image captured of the position-identification element and of the known geometrical characteristic of the position-identification element, at least one component of the orientation of a lens mounted on said frame is calculated.

\* \* \* \* \*

UNITED STATES PATENT AND TRADEMARK OFFICE
CERTIFICATE OF CORRECTION

PATENT NO. : 8,360,580 B2
APPLICATION NO. : 12/593694
DATED : January 29, 2013
INVENTOR(S) : Jean-Pierre Chauveau Page 1 of 1

It is certified that error appears in the above-identified patent and that said Letters Patent is hereby corrected as shown below:

In the Specifications

In Column 21, line 21 replace the word "DOGS" with --DOG3--

Signed and Sealed this
Seventh Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,360,580 B2  Page 1 of 1
APPLICATION NO. : 12/593694
DATED : January 29, 2013
INVENTOR(S) : Jean-Pierre Chauveau It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this
First Day of September, 2015

Michelle K. Lee
*Director of the United States Patent and Trademark Office*